US012758140B2

(12) United States Patent
Brown et al.

(10) Patent No.: US 12,758,140 B2
(45) Date of Patent: Oct. 13, 2026

(54) WIRELESS SENSORS FOR NERVE INTEGRITY MONITORING SYSTEMS

(71) Applicant: Medtronic Xomed, Inc., Minneapolis, MN (US)

(72) Inventors: Richard L. Brown, Mesa, AZ (US); John G. Pollock, Peoria, AZ (US); Jeff R. Justis, Germantown, TN (US); Kevin L. Mcfarlin, St. Johns, FL (US); Randal C. Schulhauser, Phoenix, AZ (US); Tyler S. Stevenson, Phoenix, AZ (US)

(73) Assignee: Medtronic Xomed, Inc., Minneapolis, MN (US)

(*) Notice: Subject to any disclaimer, the term of this patent is extended or adjusted under 35 U.S.C. 154(b) by 0 days.

(21) Appl. No.: 18/497,833

(22) Filed: Oct. 30, 2023

(65) Prior Publication Data

US 2024/0057930 A1 Feb. 22, 2024

Related U.S. Application Data

(60) Continuation of application No. 16/142,238, filed on Sep. 26, 2018, now Pat. No. 11,801,005, which is a
(Continued)

(51) Int. Cl.
*A61B 5/00* (2006.01)
*A61B 1/00* (2006.01)
(Continued)

(52) U.S. Cl.
CPC ........ *A61B 5/4041* (2013.01); *A61B 1/00004* (2013.01); *A61B 1/00016* (2013.01);
(Continued)

(58) Field of Classification Search
CPC ....... A61B 5/4041; A61B 5/0008; A61B 5/11; A61M 16/04
See application file for complete search history.

(56) References Cited

U.S. PATENT DOCUMENTS

| | | | |
|---|---|---|---|
| 4,265,237 | A | 5/1981 | Schwanbom et al. |
| 4,630,263 | A | 12/1986 | Townsend et al. |

(Continued)

FOREIGN PATENT DOCUMENTS

| | | | |
|---|---|---|---|
| AU | 2016244152 | A1 | 11/2017 |
| CA | 2957385 | A1 | 2/2016 |

(Continued)

OTHER PUBLICATIONS

Chinese Office Action regarding Application No. 201780071018.2, mailed Aug. 24, 2021.

(Continued)

*Primary Examiner* — Daniel L Cerioni
(74) *Attorney, Agent, or Firm* — Carter, DeLuca & Farrell, LLP

(57) ABSTRACT

A sensor including electrodes, a control module and a physical layer module. The electrodes are configured to (i) attach to a patient, and (ii) receive a first electromyographic signal from the patient. The control module is connected to the electrodes. The control module is configured to (i) detect the first electromyographic signal, and (ii) generate a first voltage signal. The physical layer module is configured to: receive a payload request from a console interface module or a nerve integrity monitoring device; and based on the payload request, (i) upconvert the first voltage signal to a first radio frequency signal, and (ii) wirelessly transmit the first radio frequency signal from the sensor to the console interface module or the nerve integrity monitoring device.

8 Claims, 25 Drawing Sheets

Related U.S. Application Data division of application No. 14/455,285, filed on Aug. 8, 2014, now Pat. No. 10,123,731.

(51) Int. Cl.

| | |
|---|---|
| ***A61B 1/267*** | (2006.01) |
| ***A61B 5/01*** | (2006.01) |
| ***A61B 5/0205*** | (2006.01) |
| ***A61B 5/11*** | (2006.01) |
| ***A61B 5/145*** | (2006.01) |
| ***A61B 5/1473*** | (2006.01) |
| ***A61B 5/296*** | (2021.01) |
| ***A61B 5/316*** | (2021.01) |
| ***A61B 5/389*** | (2021.01) |
| ***A61M 16/04*** | (2006.01) |
| ***A61N 1/36*** | (2006.01) |
| *A61B 5/024* | (2006.01) |
| *A61B 5/08* | (2006.01) |

(52) U.S. Cl.

CPC ........ *A61B 1/00036* (2013.01); *A61B 1/2673* (2013.01); *A61B 5/0002* (2013.01); *A61B 5/0004* (2013.01); *A61B 5/0008* (2013.01); *A61B 5/0024* (2013.01); *A61B 5/0084* (2013.01); *A61B 5/01* (2013.01); *A61B 5/02055* (2013.01); *A61B 5/11* (2013.01); *A61B 5/14539* (2013.01); *A61B 5/1473* (2013.01); *A61B 5/296* (2021.01); *A61B 5/316* (2021.01); *A61B 5/389* (2021.01); *A61B 5/4848* (2013.01); *A61B 5/6833* (2013.01); *A61B 5/6843* (2013.01); *A61B 5/6848* (2013.01); *A61B 5/6852* (2013.01); *A61B 5/7475* (2013.01); *A61M 16/04* (2013.01); *A61M 16/0443* (2014.02); *A61N 1/36031* (2017.08); *A61N 1/36034* (2017.08); *A61B 5/024* (2013.01); *A61B 5/0816* (2013.01); *A61B 5/1107* (2013.01); *A61B 2560/0209* (2013.01); *A61B 2562/0209* (2013.01); *A61M 2205/3569* (2013.01); *A61M 2205/3592* (2013.01); *A61M 2205/36* (2013.01); *A61M 2205/502* (2013.01); *A61M 2205/52* (2013.01); *A61M 2205/8206* (2013.01); *A61M 2230/06* (2013.01); *A61M 2230/42* (2013.01); *A61M 2230/50* (2013.01); *A61M 2230/60* (2013.01); *A61M 2230/63* (2013.01)

(56) References Cited

U.S. PATENT DOCUMENTS 5,116,332 A 5/1992 Lottick
5,767,791 A 6/1998 Stoop et al.
5,921,939 A 7/1999 Danielsson et al.
6,752,816 B2 6/2004 Culp et al.
7,216,001 B2 5/2007 Hacker et al.
7,236,822 B2 6/2007 Dobak, III
7,292,886 B1 11/2007 Kroll
7,496,407 B2 2/2009 Odderson
7,689,292 B2 3/2010 Hadzic et al.
7,789,833 B2 9/2010 Urbano et al.
7,987,001 B2 7/2011 Teichman et al.
7,993,269 B2 8/2011 Donofrio et al.
8,068,910 B2 11/2011 Gerber et al.
8,126,736 B2 2/2012 Anderson et al.
8,255,045 B2 8/2012 Gharib et al.
8,374,673 B2 2/2013 Adcox et al.
8,498,717 B2 7/2013 Lee et al.
8,515,520 B2 8/2013 Brunnett et al.
8,568,312 B2 10/2013 Cusimano Reaston et al.
8,568,317 B1 10/2013 Gharib et al.
8,594,779 B2 11/2013 Denison et al.
8,670,830 B2 3/2014 Carlson et al.
8,680,986 B2 3/2014 Costantino
8,688,237 B2 4/2014 Stanislaus et al.
8,805,527 B2 8/2014 Mumford et al.
8,886,280 B2 11/2014 Kartush
8,892,259 B2 11/2014 Bartol et al.
8,926,509 B2 1/2015 Magar et al.
8,956,418 B2 2/2015 Wasielewski et al.
8,989,855 B2 3/2015 Murphy et al.
9,031,658 B2 5/2015 Chiao et al.
9,078,671 B2 7/2015 Beale et al.
9,084,550 B1 7/2015 Bartol et al.
9,084,551 B2 7/2015 Brunnett et al.
9,204,830 B2 12/2015 Zand et al.
9,918,669 B2 3/2018 Brown et al.
10,039,915 B2 8/2018 McFarlin et al.
10,123,731 B2 11/2018 Brown et al.
10,368,793 B2 8/2019 Brown et al.
10,398,369 B2 9/2019 Brown et al.
10,849,517 B2 12/2020 Cantwell et al.
10,987,506 B2 4/2021 McFarlin et al.
11,696,719 B2 * 7/2023 Brown ................. A61B 5/7475 600/377
2002/0109621 A1 8/2002 Khair et al.
2002/0111624 A1 8/2002 Witt et al.
2003/0171747 A1 9/2003 Kanehira et al.
2003/0181798 A1 9/2003 Al-Ali
2004/0135528 A1 7/2004 Yasohara et al.
2005/0075067 A1 4/2005 Lawson et al.
2005/0075578 A1 4/2005 Gharib et al.
2005/0085743 A1 4/2005 Hacker et al.
2005/0131464 A1 6/2005 Heinrich et al.
2005/0149143 A1 7/2005 Libbus et al.
2005/0159659 A1 7/2005 Sawan et al.
2005/0215993 A1 9/2005 Phan
2005/0267529 A1 12/2005 Crockett et al.
2006/0025702 A1 2/2006 Sterrantino et al.
2006/0200219 A1 9/2006 Thrope et al.
2006/0241725 A1 10/2006 Libbus et al.
2006/0276702 A1 12/2006 McGinnis
2007/0083193 A1 4/2007 Werneth et al.
2007/0191915 A1 8/2007 Strother et al.
2007/0260293 A1 11/2007 Carpenter et al.
2007/0270678 A1 11/2007 Fadem et al.
2007/0270918 A1 11/2007 De Bel et al.
2007/0282217 A1 12/2007 McGinnis et al.
2008/0051673 A1 2/2008 Kong et al.
2008/0077198 A1 3/2008 Webb et al.
2008/0183190 A1 7/2008 Adcox et al.
2008/0183915 A1 7/2008 Tima
2008/0214903 A1 9/2008 Orbach
2008/0218393 A1 9/2008 Kuramochi et al.
2008/0300650 A1 12/2008 Gerber et al.
2008/0306348 A1 12/2008 Kuo et al.
2009/0024187 A1 1/2009 Erickson et al.
2009/0054804 A1 2/2009 Gharib et al.
2009/0157141 A1 6/2009 Chiao et al.
2009/0177112 A1 7/2009 Gharib et al.
2009/0182322 A1 7/2009 D'Amelio et al.
2009/0182328 A1 7/2009 D'Amelio et al.
2009/0182330 A1 7/2009 D'Amelio et al.
2009/0182331 A1 7/2009 D'Amelio et al.
2009/0186577 A1 7/2009 Ross et al.
2009/0240117 A1 9/2009 Chmiel et al.
2009/0299439 A1 12/2009 Mire et al.
2010/0036280 A1 2/2010 Ballegaard et al.
2010/0130913 A1 5/2010 Baynham et al.
2010/0145178 A1 6/2010 Kartush
2010/0152811 A1 6/2010 Flaherty
2010/0152812 A1 6/2010 Flaherty et al.
2010/0160731 A1 6/2010 Giovannini et al.
2010/0168561 A1 7/2010 Anderson
2010/0191311 A1 7/2010 Scheiner et al.
2010/0280568 A1 11/2010 Bulkes et al.
2011/0004207 A1 1/2011 Wallace et al.
2011/0028860 A1 2/2011 Chenaux et al.
2011/0071418 A1 3/2011 Stellar et al.
2011/0160731 A1 6/2011 Bleich et al.

(56) References Cited

U.S. PATENT DOCUMENTS

| | | | |
|---|---|---|---|
| 2011/0190596 | A1 | 8/2011 | Hacker et al. |
| 2011/0230734 | A1 | 9/2011 | Fain et al. |
| 2011/0230782 | A1 | 9/2011 | Bartol et al. |
| 2011/0230783 | A1 | 9/2011 | Bartol et al. |
| 2011/0237924 | A1 | 9/2011 | McGusty et al. |
| 2011/0245647 | A1 | 10/2011 | Stanislaus et al. |
| 2011/0270120 | A1 | 11/2011 | McFarlin et al. |
| 2011/0270121 | A1 | 11/2011 | Johnson et al. |
| 2012/0004516 | A1 | 1/2012 | Eng et al. |
| 2012/0071784 | A1 | 3/2012 | Melkent et al. |
| 2012/0245439 | A1 | 9/2012 | Andre et al. |
| 2012/0330384 | A1 | 12/2012 | Perryman et al. |
| 2013/0030257 | A1 | 1/2013 | Nakata et al. |
| 2013/0090641 | A1 | 4/2013 | McKinney et al. |
| 2013/0116678 | A1 | 5/2013 | Koss et al. |
| 2013/0245722 | A1 | 9/2013 | Ternes et al. |
| 2013/0253334 | A1 | 9/2013 | Al-Ali et al. |
| 2013/0261422 | A1 | 10/2013 | Gilmore et al. |
| 2013/0304059 | A1 | 11/2013 | Allen, IV et al. |
| 2013/0345701 | A1 | 12/2013 | Allen, IV et al. |
| 2014/0005753 | A1 | 1/2014 | Carbunaru |
| 2014/0039491 | A1 | 2/2014 | Bakos et al. |
| 2014/0058284 | A1 | 2/2014 | Bartol et al. |
| 2014/0067007 | A1 | 3/2014 | Drees et al. |
| 2014/0073985 | A1 | 3/2014 | Sakai et al. |
| 2014/0074084 | A1 | 3/2014 | Engeberg et al. |
| 2014/0275849 | A1 | 9/2014 | Acquista |
| 2014/0275914 | A1 | 9/2014 | Li et al. |
| 2014/0277259 | A1 | 9/2014 | Rosenberg et al. |
| 2014/0303452 | A1 | 10/2014 | Ghaffari |
| 2014/0316229 | A1 | 10/2014 | Tognetti et al. |
| 2014/0336635 | A1 | 11/2014 | Hart et al. |
| 2014/0364920 | A1 | 12/2014 | Doan et al. |
| 2015/0012066 | A1 | 1/2015 | Underwood |
| 2015/0088029 | A1 | 3/2015 | Wybo |
| 2015/0112325 | A1 | 4/2015 | Whitman |
| 2015/0157237 | A1 | 6/2015 | Murphy et al. |
| 2015/0173636 | A1 | 6/2015 | Mokelke et al. |
| 2015/0202395 | A1 | 7/2015 | Fromentin |
| 2015/0230749 | A1 | 8/2015 | Gharib et al. |
| 2015/0238260 | A1 | 8/2015 | Nau, Jr. |
| 2015/0250423 | A1 | 9/2015 | Hacker et al. |
| 2016/0015299 | A1 | 1/2016 | Chan et al. |
| 2016/0038072 | A1 | 2/2016 | Brown et al. |
| 2016/0038073 | A1 | 2/2016 | Brown et al. |
| 2016/0038074 | A1 | 2/2016 | Brown et al. |
| 2016/0038225 | A1 | 2/2016 | Couture et al. |
| 2016/0199659 | A1 | 7/2016 | Jiang et al. |
| 2016/0206362 | A1 | 7/2016 | Mehta et al. |
| 2016/0235999 | A1 | 8/2016 | Nuta et al. |
| 2016/0262699 | A1 | 9/2016 | Goldstone et al. |
| 2016/0270679 | A1 | 9/2016 | Mahon et al. |
| 2016/0287112 | A1 | 10/2016 | Mcfarlin et al. |
| 2016/0287861 | A1 | 10/2016 | Mcfarlin et al. |
| 2016/0317053 | A1 | 11/2016 | Srivastava |
| 2017/0202570 | A1 | 7/2017 | Shelton, IV et al. |
| 2017/0202598 | A1 | 7/2017 | Shelton, IV et al. |
| 2018/0078161 | A1 | 3/2018 | Cantwell et al. |
| 2019/0021643 | A1 | 1/2019 | Brown et al. |
| 2019/0021644 | A1 | 1/2019 | Brown et al. |

FOREIGN PATENT DOCUMENTS

| | | | |
|---|---|---|---|
| CN | 2610843 | Y | 4/2004 |
| CN | 101528303 | A | 9/2009 |
| CN | 101594830 | A | 12/2009 |
| CN | 101594906 | A | 12/2009 |
| CN | 102046098 | A | 5/2011 |
| CN | 102238904 | A | 11/2011 |
| CN | 102762251 | A | 10/2012 |
| CN | 103608069 | A | 2/2014 |
| CN | 104203129 | A | 12/2014 |
| CN | 105744887 | A | 7/2016 |
| EP | 1587418 | A1 | 10/2005 |
| GB | 2452158 | A | 2/2009 |
| JP | 2004/500217 | A | 1/2004 |
| JP | 2004/503266 | A | 2/2004 |
| JP | 2008508049 | A | 3/2008 |
| JP | 2008/519609 | A | 6/2008 |
| JP | 2008538996 | A | 11/2008 |
| JP | 2009/268016 | A | 11/2009 |
| JP | 2010515487 | A | 5/2010 |
| JP | 2011224085 | A | 11/2011 |
| JP | 2012/516205 | A | 7/2012 |
| JP | 2013/503015 | A | 1/2013 |
| JP | 2013/506507 | A | 2/2013 |
| JP | 2013505080 | A | 2/2013 |
| JP | 2013/525002 | A | 6/2013 |
| JP | 2014/117328 | A | 6/2014 |
| JP | 2014524279 | A | 9/2014 |
| JP | 2015513988 | A | 5/2015 |
| JP | 2018/514258 | A | 6/2018 |
| KR | 1020130052534 | A | 5/2013 |
| TW | 1331027 | B | 10/2010 |
| WO | 95/25472 | A1 | 9/1995 |
| WO | 99/37359 | A1 | 7/1999 |
| WO | 01/78831 | A2 | 10/2001 |
| WO | 02/082982 | A1 | 10/2002 |
| WO | 03026482 | A2 | 4/2003 |
| WO | 2004064632 | A1 | 8/2004 |
| WO | 2006/026482 | A2 | 3/2006 |
| WO | 2008/012398 | A1 | 1/2008 |
| WO | 2010/090835 | A1 | 8/2010 |
| WO | 2011035311 | A1 | 3/2011 |
| WO | 2011041684 | A2 | 4/2011 |
| WO | 2011136962 | A1 | 11/2011 |
| WO | 2011/150502 | A2 | 12/2011 |
| WO | 2012129574 | A2 | 9/2012 |
| WO | 2013/019757 | A2 | 2/2013 |
| WO | 2013/151770 | A1 | 10/2013 |
| WO | 2015-069962 | A1 | 5/2015 |
| WO | 2015123100 | A1 | 8/2015 |
| WO | 2016/160477 | A1 | 10/2016 |

OTHER PUBLICATIONS

Office Action regarding Japanese Patent Application No. 2017-552026, dated Oct. 13, 2021 (with English Translation).

Japanese Office Action regarding Japanese Patent Application No. 2020-135550, dated Dec. 28, 2021.

Korean Office Action regarding Application No. 1020197010841, dated Feb. 3, 2022.

Japanese Office Action regarding Japanese Patent Application No. 2019515506, dated Feb. 4, 2022.

Canadian Office Action regarding Canadian Application No. 3099052, dated Feb. 18, 2022.

European Office Action regarding Patent Application No. 20176316.6, dated Dec. 7, 2021.

Canadian Examination Report regarding Application No. 2,981,636, mailed Mar. 9, 2022.

Chinese Office Action regarding Patent Application No. 201780071018.2, dated Mar. 24, 2022.

Japanese Office Action regarding Patent Application No. 2019-515506, dated Apr. 22, 2022.

Japanese Office Action regarding Application No. 2020-134805, dated May 5, 2022.

Summons to Attend Oral Proceedings regarding European Patent Application No. 201763166, dated Sep. 26, 2022.

Japanese Office Action regarding Application No. 2020-134805, dated May 11, 2022.

First Office Action—Request for the submission of an Opinion, corresponding to Korean Patent Application No. 10-2017-7032060 (corresponding to PCT/US2016/023910), dated Oct. 26, 2022.

European Patent Office—Office Action corresponding to EP 17 778 021.0, dated Nov. 22, 2022.

China—Decision on Rejection, corresponding to Chinese Application No. 201780071018.2, Date of Dispatch: Sep. 23, 2022.

European Patent Office Brief Communication regarding Oral Proceedings, Date: Jan. 12, 2023, corresponding to European Application No. 20176316.3.

(56) References Cited

OTHER PUBLICATIONS

Cypress Perform. SPI-based CyFi™ Transceiver Data Sheet. Cypress Semiconductor Corporation. (Jun. 25, 2009) pp. 1-45.
International Search Report and Written Opinion for PCT/US2015/043844 mailied Jan. 12, 2016.
Wustrack "Physical Activity does not correlate with HRQL Scores in Patients with Degeneratie Lumbar Conditions" Proceedings of the NASS 20th Annual Meeting/The Spine Journal 5 (2005) IS-189S.
Wustrack "Change in Physical Activity One Year after Lumbar Decompression with or without Fusion, is it Correlated to Self-Reported Outcome Scores?" Proceedings of NASS 20th Annual Meeting/The Spine Journal 5 (2005) IS-189S.
Hurley "Physiotherapy for Sleep Disturbance in Chronic Low Pack Pain: a Feasibility Randomised Controlled Trial" BMC Musculoskeletal Disorders; 11 pages; 2010.
Invitation to Pay Additional Fees mailed Jun. 10, 2016 for International Application No. PCT/US2016/023903 which corresponds to U.S. Appl. No. 14/678,485, filed Apr. 3, 2015.
International Search Report and Written Opinion for PCT/US2016/023910 dated Aug. 5, 2016 which claims benefit of U.S. Appl. No. 14/578,452, filed Apr. 3, 2015.
International Search Report and Written Opinion for PCT/US2016/023903 dated Sep. 19, 2016 which claims benefit of U.S. Appl. No. 14/678,485, filed Apr. 3, 2015.
International Preliminary Report on Patentability mailed Oct. 12, 2017 in corresponding International Application No. PCT/US2016/023903.
International Preliminary Report on Patentability mailed Oct. 12, 2017 in corresponding/related International Application No. PCT/US2016/023910.
Australian Examination Report mailed Dec. 8, 2018 in corresponding/related Australian Application No. 2016244152.
International Search Report and Written Opinion mailed Nov. 29, 2017 in corresponding International Application No. PCT/US2017/051825.
Canadian Office Action mailed Dec. 11, 2017 in corresponding/related Canadian Application No. 2,957,385.
Australian Office Action mailed Feb. 8, 2018 in corresponding/related Australian Application No. 2015301110.
Japanese Office Action mailed Mar. 22, 2018 in corresponding/related Australian Application No. 2017-506854.
Canadian Office Action mailed Jul. 27, 2018 in corresponding/related Canadian Application No. 2,981,635.
Korean Office Action mailed Aug. 21, 2018 in corresponding/related Korean Application No. 10-2017-7006340.
Japanese Office Action mailed Nov. 26, 2018 in corresponding/related Japanese Application No. 2017-506854.
Office Action mailed Feb. 13, 2019 in corresponding/related European Application No. 15753542.8.
Office Action mailed Feb. 20, 2019 in corresponding/related Korean Application No. 10-2017-7032059.
International Preliminary Report on Patentability mailed Mar. 28, 2019 in corresponding/related International Application No. PCT/US2017/051825.
Office Action mailed Apr. 22, 2019 in corresponding/related Chinese Application No. 201580053580.3.
Office Action mailed Jun. 20, 2019 in corresponding/related Canadian Application No. 2,981,635.
Medtronic Xomed Inc. "APS Electrode Stimulator" Brochure, 10 pages, 2010.
Office Action regarding European Patent Application No. 16712713.3, dated Dec. 6, 2019.
Office Action regarding Canadian Patent Application No. 2957385, dated Dec. 12, 2019.
Office Action regarding Australian Patent Application No. 2016243081, dated Dec. 21, 2019.
Office Action regarding Chinese Patent Application No. 201580053580.3, dated Jan. 7, 2020 (with English Translation).
Office Action mailed Feb. 26, 2020 in corresponding/related Japanese Application No. 2019-050923.
Examination Report mailed Feb. 28, 2020 in corresponding/related Australian Application No. 2019201702.
Office Action mailed Feb. 5, 2020 in corresponding/related Indian Application No. 201717004436.
Office Action regarding corresponding/related Japanese Patent Application No. 2017552026, dated Mar. 27, 2020.
Office Action mailed Apr. 2, 2020 in corresponding/related Chinese Application No. 201680030281.2.
Office Action mailed Apr. 14, 2020 in corresponding/related Chinese Application No. 201680030207.0.
Office Action mailed Jun. 30, 2020 in corresponding/related Chinese Application No. 201580053580.3.
Extended European Search Report mailed Jul. 1, 2020 in corresponding/related European Application No. 20176316.6.
Office Action mailed Aug. 18, 2020 in corresponding/related Brazilian Application No. BR112017002470-5.
Office Action mailed Aug. 26, 2020 in corresponding/related Korean Application No. 10-2019-7012435.
Office Action mailed Aug. 26, 2020 in corresponding/related Korean Application No. 10-2020-7007858.
Office Action mailed Sep. 16, 2020 in corresponding/related Chinese Application No. 201680030207.0.
Examination Report mailed Sep. 8, 2020, in corresponding/related Australian Application No. 2019203347.
Examination Report mailed Sep. 8, 2020, in corresponding/related Australian Application No. 2019203348.
Office Action mailed Nov. 3, 2020, in corresponding/related Canadian Application No. 2,957,385.
Office Action mailed Nov. 10, 2020 in corresponding/related Japanese Application No. Japanese Patent Appln. No. 2017-552026.
Pre-Appeal Examination Report regarding Japanese Patent Application No. 2017-552026, dated Feb. 16, 2021.
Office Action regarding Chinese Patent Application No. 201580053580.3, dated Mar. 1, 2021.
Office Action regarding European Patent Application No. 16715204.0, dated May 21, 2021.
Rich Vogel, Understanding Anodal and Cathodal Stimulation, The ASNM Monitor, 2017, https://www.asnm.org/blogpost/1635804/290597/Understanding-Anodal-and-Cathodal-Stimulation.
Office Action regarding Japanese Patent Application No. 2020-134805, dated Jul. 13, 2021 with English translation.
Office Action regarding Japanese Patent Application No. 2020-135550, dated Jul. 5, 2021 with English translation.

* cited by examiner

WIRELESS SENSORS FOR NERVE INTEGRITY MONITORING SYSTEMS

CROSS-REFERENCE TO RELATED APPLICATIONS

This application is a continuation of U.S. application Ser. No. 16/142,238 filed on Sep. 26, 2018, now U.S. Pat. No. 11,801,005, which is a division of U.S. application Ser. No. 14/455,285 filed on Aug. 8, 2014, now U.S. Pat. No. 10,123,731. The entire disclosures of the above applications are incorporated herein by reference.

FIELD

The present disclosure relates to nerve integrity monitoring systems and devices.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

A nerve integrity monitoring (NIM) system can include a stimulation probe device, sensors, an electrode connection box, and an electromyography (EMG) monitoring device. The stimulation probe device is used to stimulate nerve and/or muscle activity. As an example, a stimulation probe device may include a stimulating electrode tip. A surgeon may touch a location on a patient with the electrode tip to provide a voltage and/or current to a location on the patient and stimulate nerve activity and as a result a muscle response (or muscle activity). A reference patch may be attached to the patient away from (i) the sensors, and (ii) an area being stimulated. An electrode of the reference patch can be at a reference potential. The sensors can include electrodes that are attached to the patient and used to monitor the muscle activity. A voltage potential between the electrode tip of the stimulation probe device and the reference patch and voltage potentials indicated by outputs of the sensors may be provided via wires to the electrode connection box. The wires are plugged into respective jacks in the electrode connection box.

The electrode connection box can have channels respectively for: a voltage potential of the stimulation probe device; a voltage potential of the reference patch; and output voltages of the sensors. The electrode connection box may filter signals received from the stimulation probe device and sensors and provide corresponding signals to the EMG monitoring device. Depending on the surgical procedure being performed, a large number of cables may be used to transmit information between (i) the stimulation probe device and sensors and (ii) the electrode connection box. As an example, 1-32 channels may be used during a surgical procedure. Each of the channels may correspond to a respective twisted pair cable (each cable having a twisted pair of wires). Each of the cables connected to the sensors is secured to a patient via the electrodes of the sensors, extends away from the patient, and is routed outside of a sterile field (or environment) in which the patient is located to the EMG monitoring device.

In one example, a certain type of sensor may be used during thyroid surgery to monitor nerves in intrinsic laryngeal musculature of a patient. Injury to a recurrent laryngeal nerve (RLN) is one of the most serious complications of thyroid surgery. An endotracheal tube can be used during thyroid surgery to open an airway and provide air to lungs of the patient. The endotracheal tube can include electrodes that are designed to contact vocal chords of the patient to facilitate EMG monitoring of the vocal chords during surgery.

As an example, a stimulating electrode may be placed on a vagus nerve in the neck of the patient to deliver continuous low-level stimulation to nerve endings. A baseline of nerve function is obtained and subsequent EMG responses are monitored via the electrodes connected to the endotracheal tube. Electromyographic signals are generated and detected by the electrodes and provided to an EMG monitoring device. The EMG monitoring device monitors changes in the electromyographic signals to detect changes in intrinsic laryngeal musculature of the patient. Between stimulations, nerves can be at risk due to surgical incision, and/or “blind” trauma caused by stretching, heating, compressing, and/or manipulating tissues of a patient during tumor/thyroid removal. The EMG responses are charted in real time to provide feedback with regard to the conditions of the nerves.

SUMMARY

A sensor is provided and includes electrodes, a control module and a physical layer module. The electrodes are configured to (i) attach to a patient, and (ii) receive a first electromyographic signal from the patient. The control module is connected to the electrodes. The control module is configured to (i) detect the first electromyographic signal, and (ii) generate a first voltage signal. The physical layer module is configured to: receive a payload request from a console interface module or a nerve integrity monitoring device; and based on the payload request, (i) upconvert the first voltage signal to a first radio frequency signal, and (ii) wirelessly transmit the first radio frequency signal from the sensor to the console interface module or the nerve integrity monitoring device.

In other features, a method is provided and includes: receiving, at a sensing module, a first electromyographic signal from a patient via electrodes, wherein the sensing module is directly connected to the electrodes; generate a first voltage signal based on the electromyographic signal; generate a first voltage signal based on the electromyographic signal; upconverting the first voltage signal to a first radio frequency signal; and based on the payload request, wirelessly transmitting the first radio frequency signal from the sensing module to the console interface module or the nerve integrity monitoring device.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

In the drawings, reference numbers may be reused to identify similar and/or identical elements.

DESCRIPTION

Any clutter and/or time inefficiencies in an operating room that can be eliminated and/or minimized is advantageous to both hospital personal and a patient. Nerve integrity monitoring (NIM) systems currently have extensive cabling. Most of the cabling corresponds to transporting or delivery evoked response signals from sensors to a NIM device, as a result of stimulated nerve activity in muscles of a patient. Various techniques are disclosed below, which reduce and/or eliminate cables used in a NIM system, reduce and/or minimize certain time inefficiencies associated with current NIM systems, and minimize power consumption.

Figure 1:
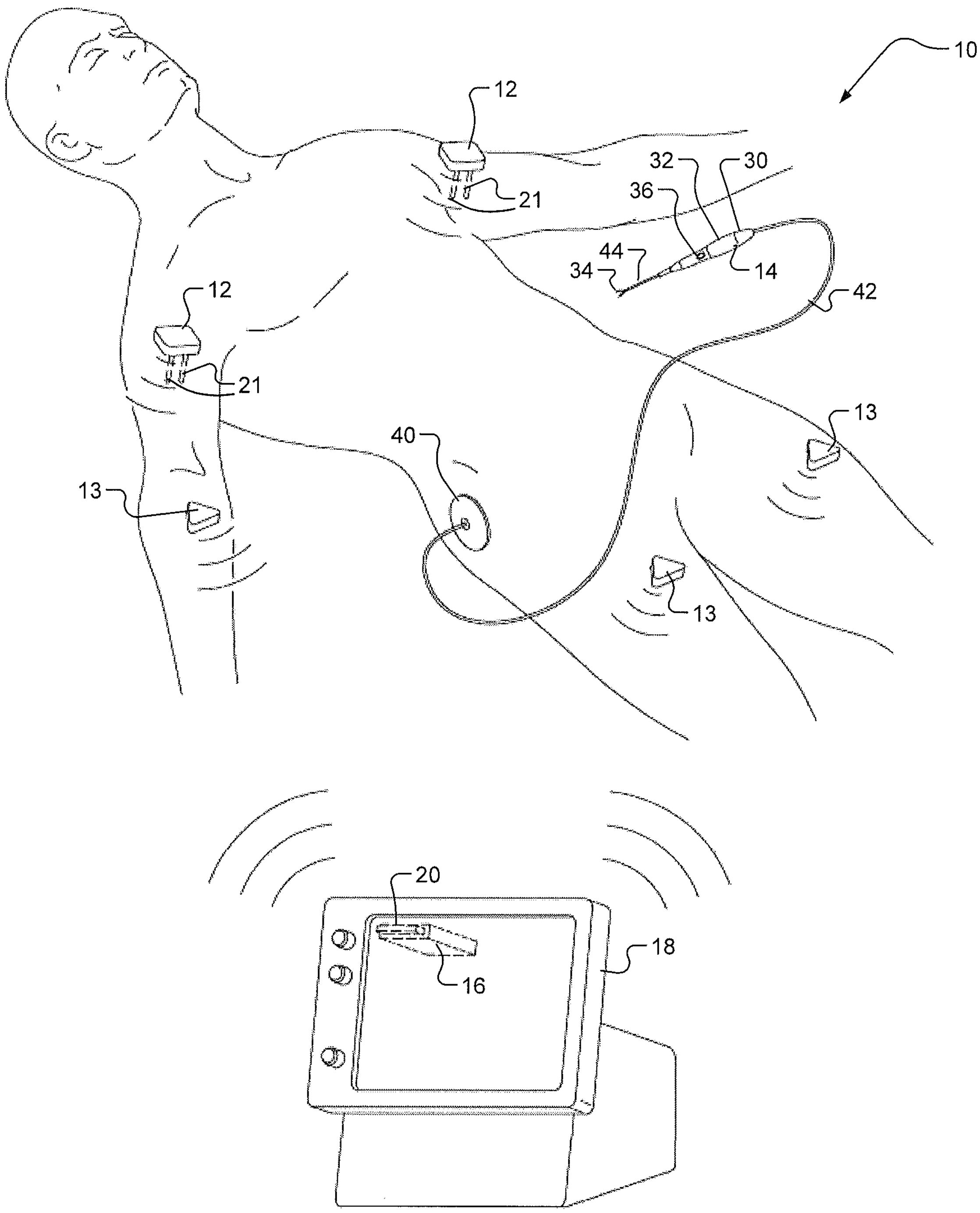
FIG. 1 is a perspective view of a wireless nerve integrity monitoring (WNIM) system in accordance with the present disclosure.
Figure 2:
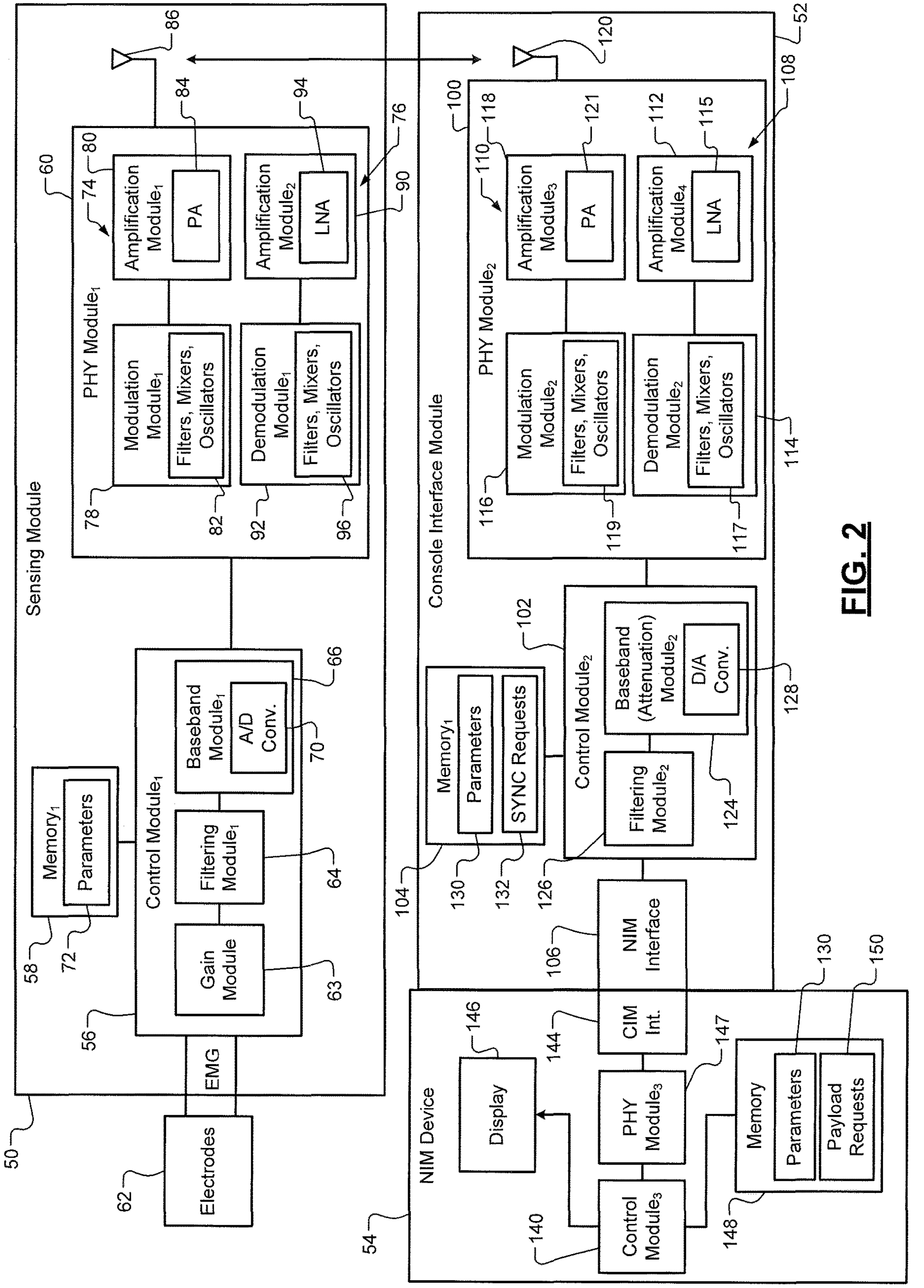
FIG. 2 is a functional block diagram of a sensing module, a console interface module and a NIM device in accordance with the present disclosure.

FIG. 1 shows a wireless nerve integrity monitoring (WNIM) system 10. The WNIM system 10, as shown, includes sensors 12, 13, a stimulation probe device 14, a wireless interface adaptor (WIA) 16 and a NIM device 18. The WIA 16 includes a console interface module (CIM), which is shown in FIG. 2, and an interface 20 (e.g., a 32-pin connector) for connecting to the NIM device 18. The WIA 16 is shown as being plugged into a back side of the NIM device 18. Although the WIA 16 is shown as being plugged into the NIM device 18 via the interface 20, the WIA 16 may be separate from the NIM device 18 and wirelessly communicate with the NIM device 18. The sensors 12, 13 and the stimulation probe device 14 wirelessly communicate with the CIM and/or the NIM device 18. In one embodiment, the WIA 16 is connected to the NIM device 18 and wirelessly communicates with the sensors 12, 13 and the stimulation probe device 14. Information described below as being transmitted from the NIM device 18 to the CIM may then be relayed from the CIM to the sensors 12, 13 and/or the stimulation probe device 14. Information and/or data described below as being transmitted from the sensors 12, 13 and/or the stimulation probe device 14 to the CIM may then be relayed from the CIM to the NIM device 18.

The WIA 16: transfers signals between (i) the NIM device 18 and (ii) the sensors 12, 13 and the stimulation probe device 14; and/or adds additional information to the signals received from the NIM device 18 prior to forwarding the signals to the sensors 12, 13 and/or stimulation probe device 14, as described below. The WIA 16 may: operate essentially as a pass through device; be a smart device and add and/or replace information provided in received signals; and/or generate signals including determined information based on received signals. For example, the WIA 16 may receive a payload request signal from the NIM device 18 and determine a delay time between when the payload request was received and when a next synchronization (SYNC) request signal is to be transmitted. This is described in further detail with respect to FIGS. 18 and 22. The WIA 16 allows the NIM device 18 to be compatible with legacy hardware. The WIA 16 may be unplugged from the NIM device 18 and a traditional electrode connection box may be connected to the WIA 16 using the same interface of the NIM device 18 as the WIA 16. The WIA 16 replaces cables traditionally connected between (i) a NIM device 18 and (ii) sensors 12, 13 and a stimulation probe device 14. This eliminates wires traversing (extending from within to outside) a sterile field in which a patient is located.

As another example, the WIA 16 may receive signals from the sensors 12, 13 and/or the stimulation probe device 14. The signals from the sensors 12, 13 and/or the stimulation probe device 14 may indicate voltages, current levels, durations, amplitudes, etc. and/or the WIA device 16 may determine, for example, durations and amplitudes based on the received signals. The received signals and/or the determined information may be forwarded to the NIM device 18 for evaluation and/or for display on the screen of the NIM device 18.

Although two types of sensors 12, 13 are shown in FIG. 1, other types of sensors may be incorporated in the WNIM system 10. Another type of sensor is shown and described with respect to FIGS. 8-13. The sensors 12 of the first type are referred to as pin sensors and include respective pairs of pins 21 (or needles) that are inserted into, for example, muscle tissue of a patient. The sensors 13 of the second type are referred to as surface sensors and are adhered to skin of a patient over, for example, muscle tissue. The pin sensors 12 may, for example, be used to detect voltage potentials between the respective pairs of pins 21 of the pin sensors 12. The surface sensors 13 may, for example, be used to detect voltage potentials between respective pads of the surface sensors 13. The pin sensors 12 may each include two pins as shown or may include a different number of pins. The pins may be referred to as electrodes. Each of the surface sensors 13 may include two or more pads. The pads may be referred to as electrodes.

Figure 7A:
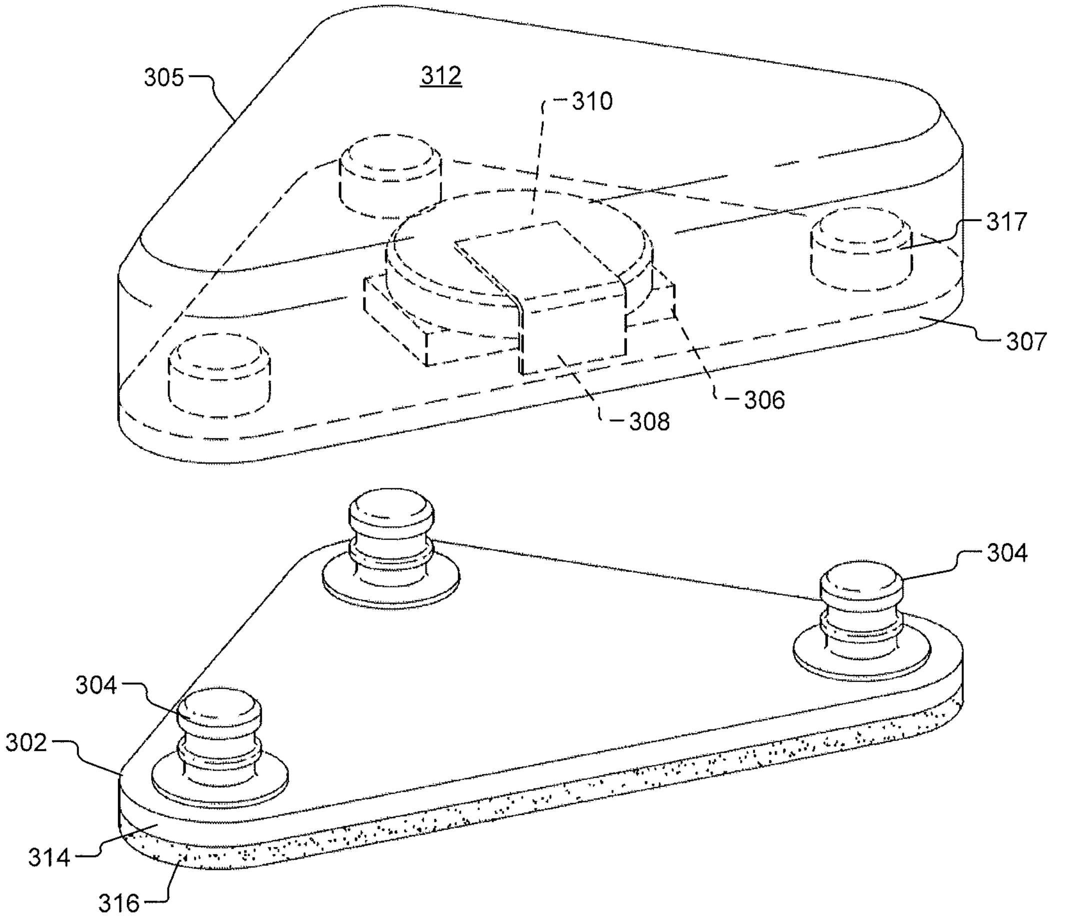
FIG. 7A is a perspective view of a three-pad sensor with an electronic control module assembly in accordance with the present disclosure.
Figure 7B:
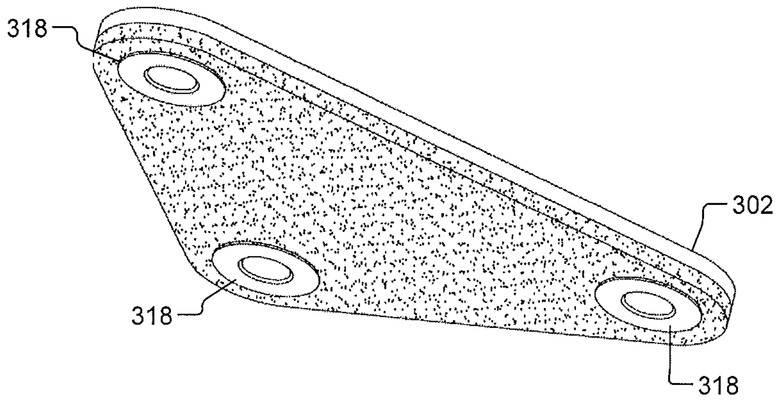
FIG. 7B is a bottom perspective view of a portion of the three-pad sensor of FIG. 7A without the electronic control module assembly and illustrating corresponding contact pads.
Figure 8:
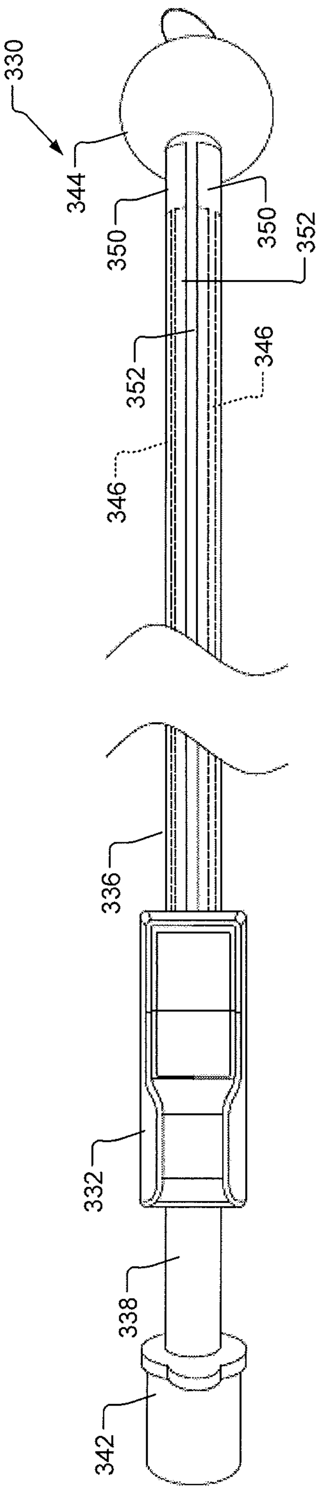
FIG. 8 is a perspective view of an EMG endotracheal tube assembly in accordance with the present disclosure.
Figure 9:
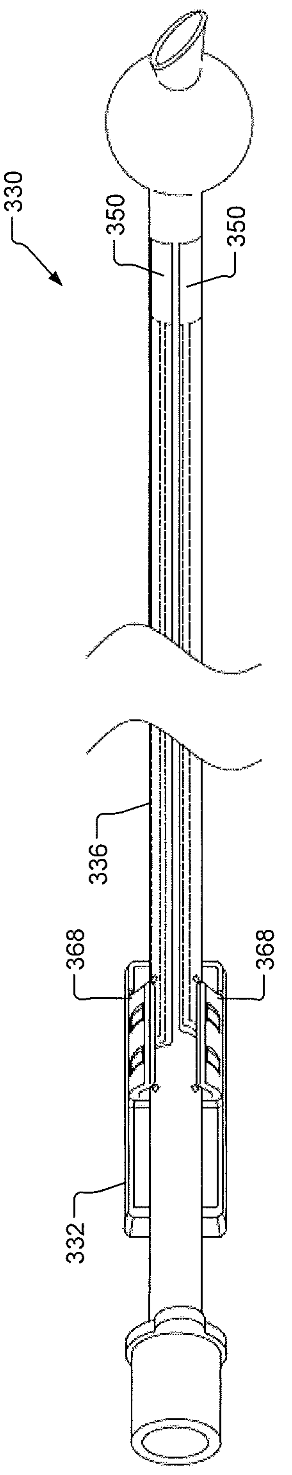
FIG. 9 is another perspective view of the EMG endotracheal tube assembly of FIG. 8.
Figure 10:
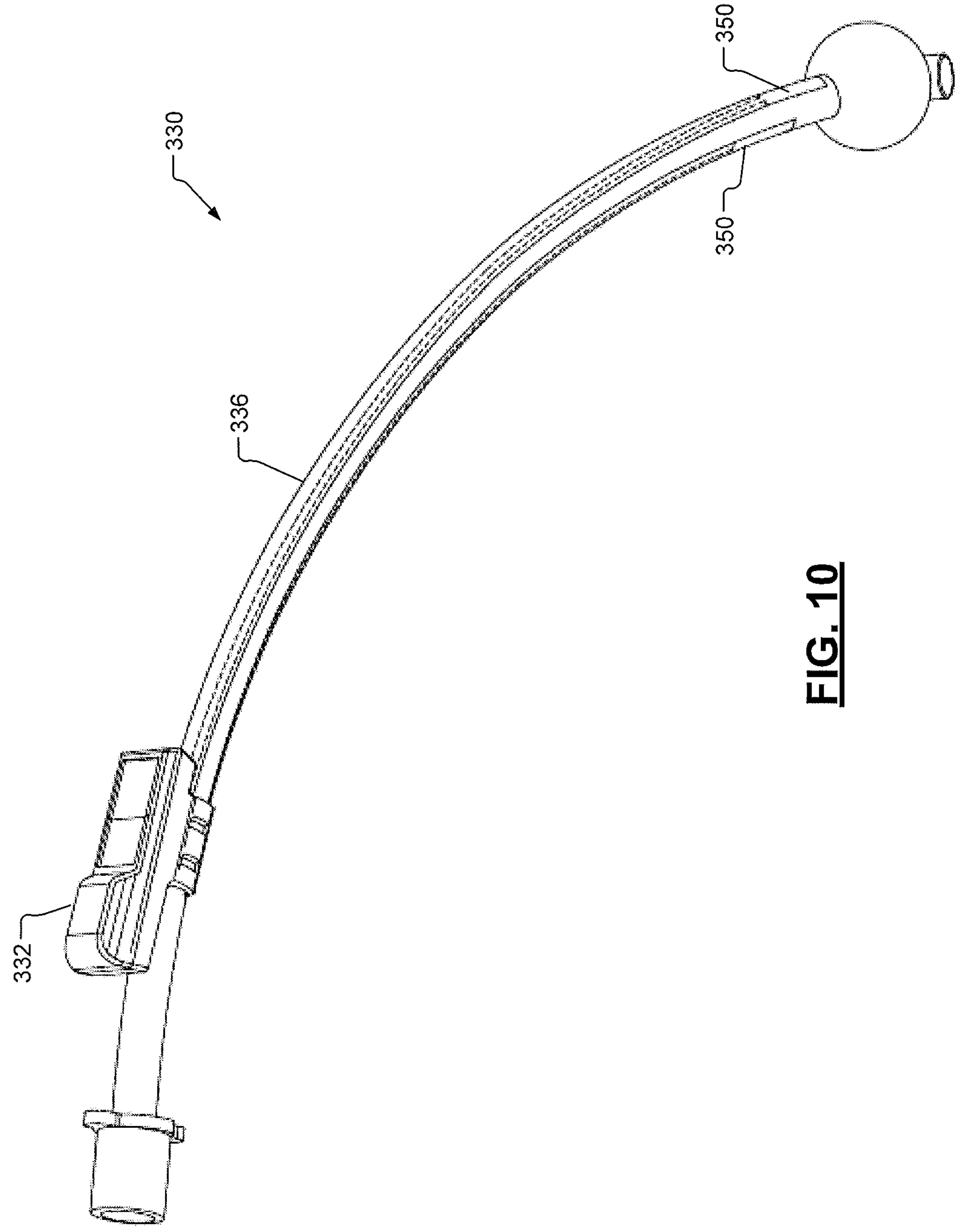
FIG. 10 is another perspective view of the EMG endotracheal tube assembly of FIG. 8.

One or more of the sensors 12, 13 may include a third electrode (pin or pad), as is further described with respect to FIGS. 7A-7B. The sensors 12, 13 are used to digitize nerve and/or muscle activity and wirelessly transmit this information to the CIM and/or the NIM device 18. The sensors 12, 13 may alert the CIM and/or the NIM device 18 of bursts (e.g., increases in voltages of evoked response signals) in nerve and/or muscle activity. An evoked response signal refers to a signal generated in a tissue of a patient as a result of a stimulation signal generated by the stimulation probe device 14.

Figure 3:
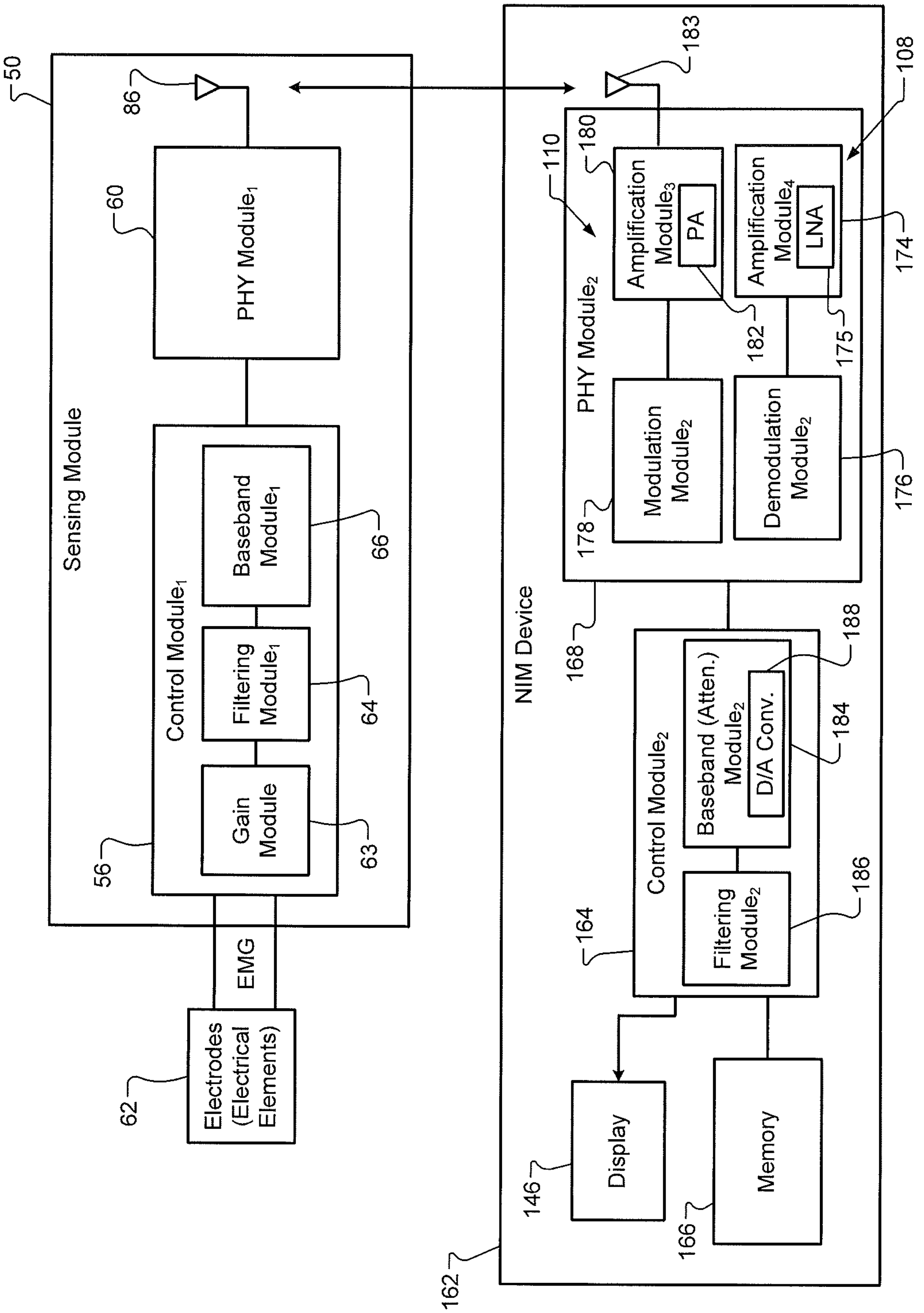
FIG. 3 is a functional block diagram of another sensing module and another NIM device in accordance with the present disclosure.
Figure 5:
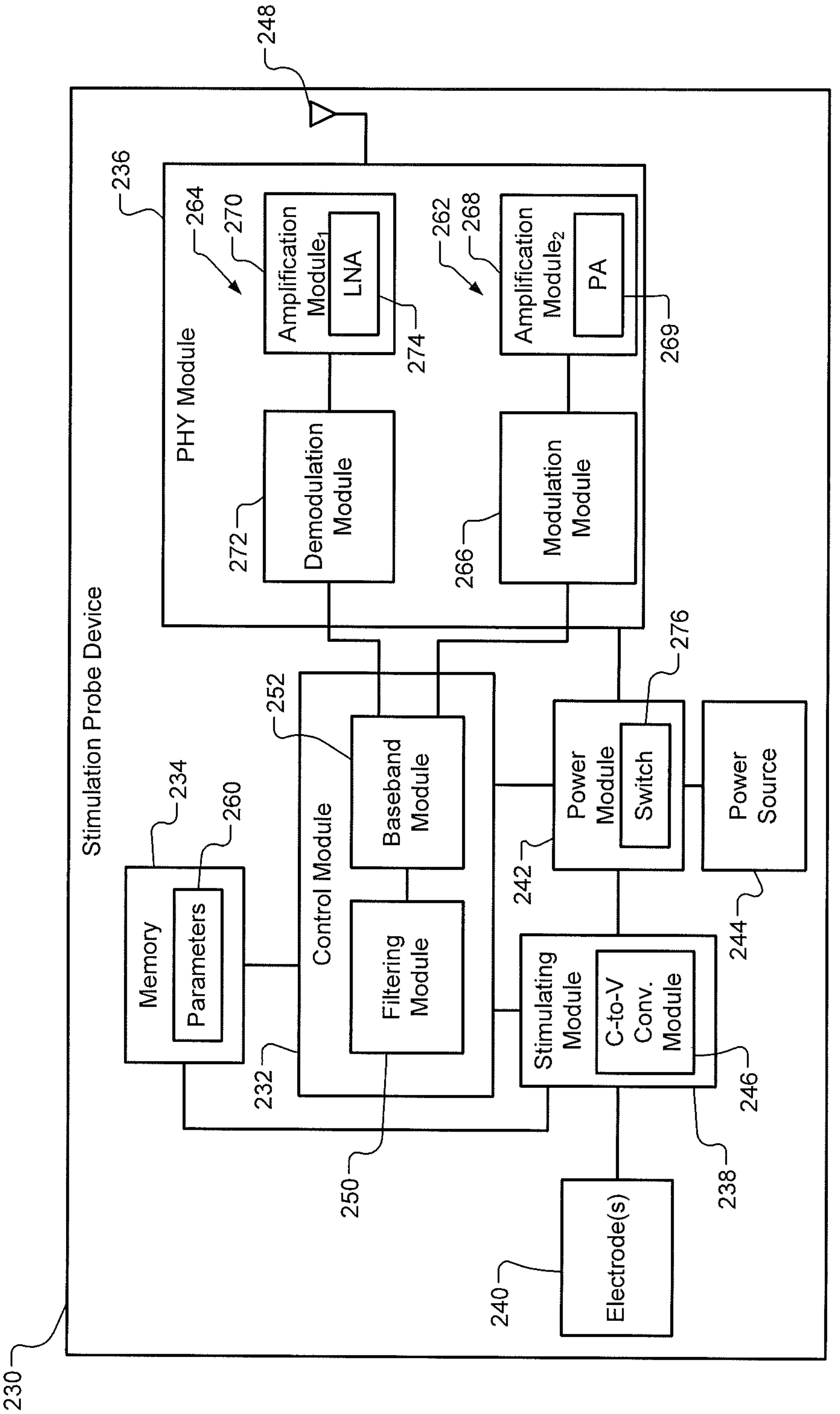
FIG. 5 is a functional block diagram of a stimulation probe device in accordance with the present disclosure.
Figure 14:
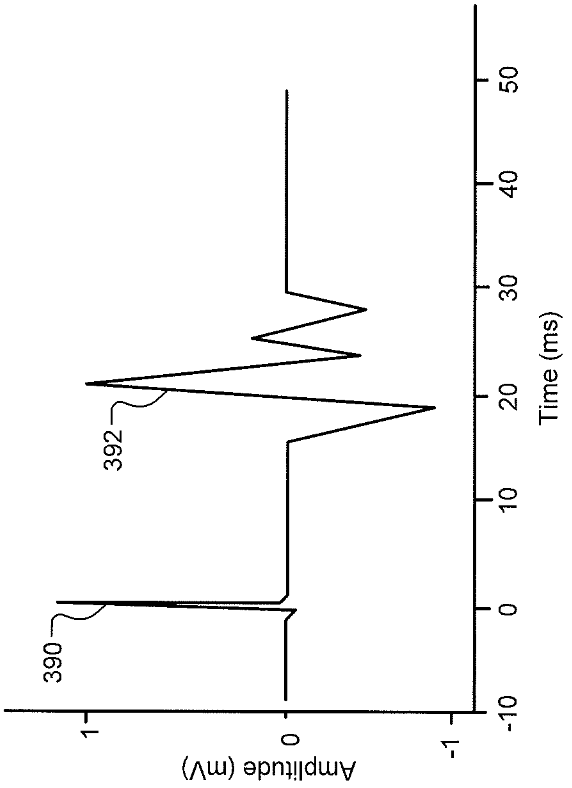
FIG. 14 is a plot of a stimulation pulse and a corresponding evoked response signal.

The stimulation probe device 14 is used to stimulate nerves and/or muscle in the patient. The stimulation probe device 14 includes: a housing 30 with a grip 32; one or more electrodes 34 (shown having two electrodes); a switch 36; a control module (an example of which is shown in FIG. 5); and an input 38 for connection to a reference pad (or patch) 40, via a cable 42. Although the stimulation probe device 14 is shown having a bifurcated tip with two electrodes 34, the stimulation probe device 14 may have one or more electrodes 34. The electrodes 34 are separated and insulated from each other and may extend within a tube 44 to the housing 30. The switch 36 may be used to turn ON the stimulation probe device 14 and/or to apply a stimulation pulse to the electrodes 34. An example of a stimulation pulse is shown in FIG. 14. The stimulation pulse may be manually generated by actuating the switch 36 or may be generated via the NIM device 18 and/or the WIA 16 via the CIM. The NIM device 18 and/or the CIM may signal the control module of the stimulation probe device 14 to generate one or more stimulation pulses to stimulate one or more nerves and/or muscles in proximity of the electrodes 34. The reference patch 40 is used to provide a reference voltage potential. One or more voltage potentials between one or more of the electrodes 34 and the reference patch 40 may be determined by: the control module of stimulation probe device 14; a control module of the NIM device 18 (examples of which are shown in FIGS. 2-3); and/or a control module of the CIM (examples of which are shown in FIGS. 2-3).

The stimulation probe device 14 may wirelessly transmit information to the CIM and/or NIM device 18. The information may include: timing information; voltage potentials between the electrodes 34; voltage potentials between the reference patch 40 and one or more of the electrodes 34; number of stimulation pulses; pulse identifiers (IDs); voltages and current levels of stimulation pulses generated; and amplitudes, peak magnitudes and/or durations of stimulation pulses generated. The timing information may include: start and end times of stimulation pulses; durations of stimulation pulses; and/or time between stimulation pulses.

In another embodiment, the WIA 16 is not included in the WNIM system 10. In this embodiment, the NIM device 18 wirelessly communicates directly with the sensors 12, 13 and the stimulation probe device 14. This may include communication with the sensors 12, 13 and the stimulation probe device 14 shown in FIG. 1 and/or communication with other sensors (e.g., the sensor shown in FIGS. 8-13) and/or stimulation devices. The WNIM system 10 may include any number of sensors and/or stimulation probe devices.

Referring now to FIG. 1 and FIG. 2, which shows a sensing module 50, a CIM 52 and a NIM device 54. The sensing module 50 wirelessly communicates with the CIM 52 and/or with the NIM device 54 via the CIM 52. The sensing module 50 may be included in any of the sensors disclosed herein including the sensors shown in FIG. 1, 7A-7B and 8-13. The CIM 52 may be included in the WIA 16 of FIG. 1.

The sensing module 50 includes a control module 56 (e.g., a microprocessor), a memory 58, and a physical layer (PHY) module 60 (e.g., a transceiver and/or radio). The control module 56 detects electromyographic signals generated in tissue of a patient via electrodes 62 (e.g., pins or pads). The electromyographic signals may be in the form of voltage signals having voltage potentials. The control module 56 includes a gain module 63 (e.g., an amplifier), a filtering module 64 (e.g., one or more filters) and a baseband module 66. The baseband module 66 may include an upconverter and a downconverter. The gain module 63 amplifies the electromyographic signals to generate amplified signals. The filtering module 64 may operate as a bandpass filter and filter out (i) frequencies of the amplified signals outside of predetermined frequency range, and (ii) a direct current (DC) voltage. This can eliminate and/or minimize noise, such as 60 Hz noise. The filtering module 64 generates a baseband signal.

The baseband module 66 may include an analog-to-digital (A/D) converting module 70 (e.g., an A/D converter) and convert the baseband signal (an analog signal) from the filtering module 64 to a digital baseband (BB) signal. The BB module 66 and/or the A/D converting module 70 may sample the output of the filtering module 64 at a predetermined rate to generate frames, which are included in the digital BB signal. By A/D converting signals at the sensor as opposed to performing an A/D conversion at the CIM 52 or the NIM device 54, opportunities for signal interference is reduced.

The BB module 66 may then upconvert the digital BB signal to an intermediate frequency (IF) signal. The BB module 66 may perform direct-sequence spread spectrum (DSSS) modulation during upconversion from the digital BB signal to the IF signal. The BB module 66 may include a mixer and oscillator for upconversion purposes. The BB module 66 and/or the control module 56 may compress and/or encrypt BB signals transmitted to the PHY module 60 prior to upconverting to IF signals and/or may decompress and/or decrypt signals received from the PHY module 60.

The BB module 66 may provide a received signal strength indication (RSSI) indicating a measured amount of power present in a RF signal received from the CIM 52. This may be used when determining which of multiple CIMs the sensor is to communicate with. The control module 56 may select a CIM corresponding to a SYNC request signal and/or a payload request signal having the most power and/or signal strength. This may include (i) selecting a channel on which the SYNC request signal and/or the payload request signal was transmitted, and (ii) communicating with the CIM on that channel. This allows the control module 56 to select the closest and proper CIM. This selection may be performed when the sensor has not previously communicated with a CIM, is switching to a different WNIM network, and/or has been reset such that the sensor does not have a record of communicating with a CIM. In one embodiment, the sensors are unable to be reset.

The memory 58 is accessed by the control module 56 and stores, for example, parameters 72. The parameters 72 may include parameters provided in SYNC request signals and/or parameters associated with electromyographic signals generated via the electrodes. The parameters associated with electromyographic signals may include voltages, current levels, amplitudes, peak magnitudes, pulse durations, etc.

The PHY module 60 includes a transmit path 74 (or transmitter) and a receiver path 76 (or receiver). The transmit path 74 includes a modulation module 78 (e.g., a modulator) and an amplification module 80 (e.g., an amplifier). The modulation module 78 modulates and upconverts the IF signal to generate a radio frequency (RF) signal. This may include Gaussian frequency-shift keying (GFSK) modulation. The modulation module 78 may include, for example, a filter, a mixer, and an oscillator (collectively identified as 82). The amplification module 80 may include a power amplifier 84, which amplifies the RF signal and transmits the RF signal via the antenna 86.

The receiver path 76 includes a second amplification module 90 and a demodulation module 92 (e.g., a demodulator). The amplification module 90 may include a low-noise amplifier (LNA) 94. The second amplification module 90 amplifies RF signals received from the CIM 52. The demodulation module 92 demodulates the amplified RF signals to generate IF signals. The IF signals are provided to the BB module 66, which then downconverts the IF signals to BB signals. The demodulation module 92 may include, for example, a filter, a mixer, and an oscillator (collectively identified as 96). The A/D converting module 70 may include a digital-to-analog (D/A) converter to convert the BB signals to analog signals. The RF signals received from the CIM 52 may include, for example, SYNC request signals or portions thereof, as further described below. Examples of information included in the SYNC request signals is shown and described below with respect to Tables 1-4.

The CIM 52 includes a PHY module 100, a control module 102, a memory 104, and a NIM interface 106 (e.g., 32 pin connector). The PHY module 100 includes a receive path (or receiver) 108 and a transmit path (or transmitter) 110. The receive path 108 includes an amplification module 112 and a demodulation module 114. The amplification module 112 amplifies RF signals received from the sensing module 50 and/or from other sensor modules and/or stimulation probe devices. The amplification module 112 may include a LNA 115. The demodulation module 114 demodulates and downconverts the amplified RF signals to generate IF signals. The demodulation module 114 may include a filter, mixer, and an oscillator (collectively referred to as 117). The transmit path 110 includes a modulation module 116 and an amplification module 118. The modulation module 116 modulates and upconverts IF signals from the control module 102 to generate RF signals. This may include Gaussian frequency-shift keying (GFSK) modulation. The modulation module 116 may include, for example, a filter, a mixer, and an oscillator (collectively identified as 119). The amplification module 118 transmits the RF signals to the sensing module 50 via an antenna 120 and/or to other sensor modules and/or stimulation probe devices. The amplification module 118 may include a power amplifier 121.

The control module 102 includes a BB module 124 and a filtering module 126. The BB module 124 converts IF signals received from the PHY module 100 to BB signals and forwards the BB signals to the filtering module 126. The BB module 124 also converts BB signals from the filtering module 126 to IF signals, which are forwarded to the modulation module 116. The BB module 124 may include a D/A converting module 128. The D/A converting module 128 may include an A/D converter to convert analog signals from the filtering module 126 to digital signals. The D/A converting module 128 may include a D/A converter to convert digital signals from the PHY module 100 to analog signals. In one embodiment, the BB module 124 does not include the D/A converting module 128 and digital signals are passed between the filtering module 126 and the PHY module 100. The BB module 124 may attenuate signals received from the demodulation module 114 to have amplitudes similar to amplitudes of signals received at the gain module 63 and/or the filtering module 64 of the sensing module 50. The filtering module 126 may be a bandpass filter and remove frequencies of signals outside a predetermined range and/or DC signals. This can eliminate and/or minimize noise, such as 60 Hz noise. The BB module 124 and/or the control module 102 may compress and/or encrypt signals transmitted to the modulation module 116 and/or decompress and/or decrypt signals received from the demodulation module 114. Although the CIM 52 is shown as being connected to the NIM device 54 via the NIM interface 106, the CIM 52 may be separate from the NIM device 54 and wirelessly communicate with the NIM device 54 via the PHY module 100.

The memory 104 is accessed by the control module 102 and stores, for example, parameters 130. The parameters 130 may include parameters provided in SYNC request signals and/or parameters associated with electromyographic signals received via the electrodes 62. The parameters 130 associated with electromyographic signals may include voltages, current levels, amplitudes, peak magnitudes, pulse durations, etc. and may include or be the same as the parameters 72. The memory may also store synchronization requests 132, which are defined below.

The NIM device 54 may include a control module 140, a PHY module 142, a CIM interface 144, a display 146 and a memory 148. The control module 140: generates payload request signals; receives data payload signals from the sensing module 50 and/or other sensing modules and stimulation probe devices via the CIM 52; and displays electromyographic signals and/or other related information on the display 146. The PHY module 142 may transmit signals to and receive signals from the control module 140 via the interfaces 106, 144 as shown or wirelessly via an antenna (not shown). The memory 148 is accessed by the control module 140 and stores the parameters 130 and may store payload requests 150, which are defined below.

The control modules 56, 126, the BB modules 66, 128, the PHY modules 60, 100, and/or one or more modules thereof control timing of signals transmitted between the sensing module 50 and the CIM 52. This is described in further detail below with respect to FIGS. 15-19 and 22. The PHY modules 60, 100 may communicate with each other in a predetermined frequency range. As an example, the PHY modules 60, 100 may communicate with each other in 2.0-3.0 giga-hertz (GHz) range. In one embodiment, the PHY modules 60, 100 transmit signals in a 2.4-2.5 GHz range. The PHY modules 60, 100 may communicate with each other via one or more channels. The PHY modules 60, 100 may transmit data at predetermined rates (e.g., 2 megabits per second (Mbps)). The CIM 52 and/or the NIM device 54 may set the frequency range, the number of channels, and the data rates based on: the number of sensor modules in and actively communicating in the WNIM system 10; the number of stimulation probe devices in and actively communicating in the WNIM system 10; the types of the sensors; the number of channels per sensor; the speed per channel of each of the sensors; the number of channels per stimulation probe device, and/or the speed per channel of the stimulation probe devices.

Referring now to FIG. 1 and FIG. 3, which shows the sensing module 50 and a NIM device 162. The sensing module 50 includes the control module 56, the memory 58 and the PHY module 60. The control module 56 includes the gain module 63, the filtering module 64 and the BB module 66. The control module 56 detects electromyographic signals via the electrodes 62. The control module 56 reports data associated with the electromyographic signals to the NIM device 162 via the PHY module 60. The control module 56 also receives signals (e.g., synchronization request signals) from the NIM device 162 via the PHY module 60.

The NIM device 162 includes a control module 164, a memory 166, a PHY module 168, and the display 146. Functionality of the CIM 52 of FIG. 2 is included in the NIM device 162. The PHY module 168 includes a receive path 170 (or receiver) and a transmit path 172 (or transmitter). The receive path 170 includes an amplification module 174 and a demodulation module 176. The amplification module 174 via a LNA 175 amplifies RF signals received from the sensing module 50 and/or from other sensor modules and/or stimulation probe devices. The demodulation module 176 demodulates and downconverts the amplified RF signals to generate IF signals. The transmit path 172 includes a modulation module 178 and an amplification module 180. The modulation module 178 and the amplification module 180 may operate similar to the modulation module 116 and the amplification module 118. The amplification module 118 may include a power amplifier 182 and transmits RF signals via an antenna 183 to the sensing module 50 and/or to other sensor modules and/or stimulation probe devices.

The control module 164 includes a BB module 184 and a filtering module 186. The BB module 184 converts IF signals received from the PHY module 168 to BB signals and forwards the BB signals to the filtering module 186. The BB module 184 also converts BB signals from the filtering module 186 to IF signals, which are forwarded to the modulation module 178. The BB module 184 may include a D/A converting module 188. The D/A converting module 188 may include an A/D converter to convert analog signals from the filtering module 186 to digital signals. The D/A converting module 188 may include a D/A converter to convert digital signals from the PHY module 168 to analog signals. In one embodiment, the BB module 184 does not include the D/A converting module 188 and digital signals are passed between the filtering module 186 and the PHY module 168. The BB module 184 may attenuate signals received from the demodulation module 176 to have amplitudes similar to amplitudes of signals received at the gain module 63 and/or the filtering module 64 of the sensing module 50. The filtering module 186 may be a bandpass filter and remove frequencies of signals outside a predetermined range and/or DC signals. This can eliminate and/or minimize noise, such as 60 Hz noise. The BB module 184 and/or the control module 164 may compress and/or encrypt signals transmitted to the modulation module 178 and/or decompress and/or decrypt signals received from the demodulation module 176.

Referring now to FIGS. 2-3, the BB module 66 of the sensing module 50 may provide a received signal strength indication (RSSI) indicating a measured amount of power present in a RF signal received from the NIM device 162. This may be used when determining which of multiple NIM devices to communicate with. The control module 56 may select a NIM device corresponding to a SYNC request signal and/or a payload request signal that has the most power and/or signal strength. This may include selecting a channel on which the SYNC request signal and/or the payload request signal was transmitted and communicating with the CIM 52 and/or the NIM device 162 on that channel. This allows the control module 56 to select the closest and proper NIM device. This selection may be performed when the corresponding sensor has not previously communicated with the NIM device 162 and/or other NIM devices and/or has been reset such that the sensor does not have a record of communicating with the NIM device 162 and/or other NIM devices.

The memory 166 may store the parameters 130, the payload requests 150 and/or the SYNC requests 132. The memory 166 may store the SYNC requests and may not store the payload requests. This is because the NIM device 162 may generate SYNC requests and not payload requests.

Figure 4:
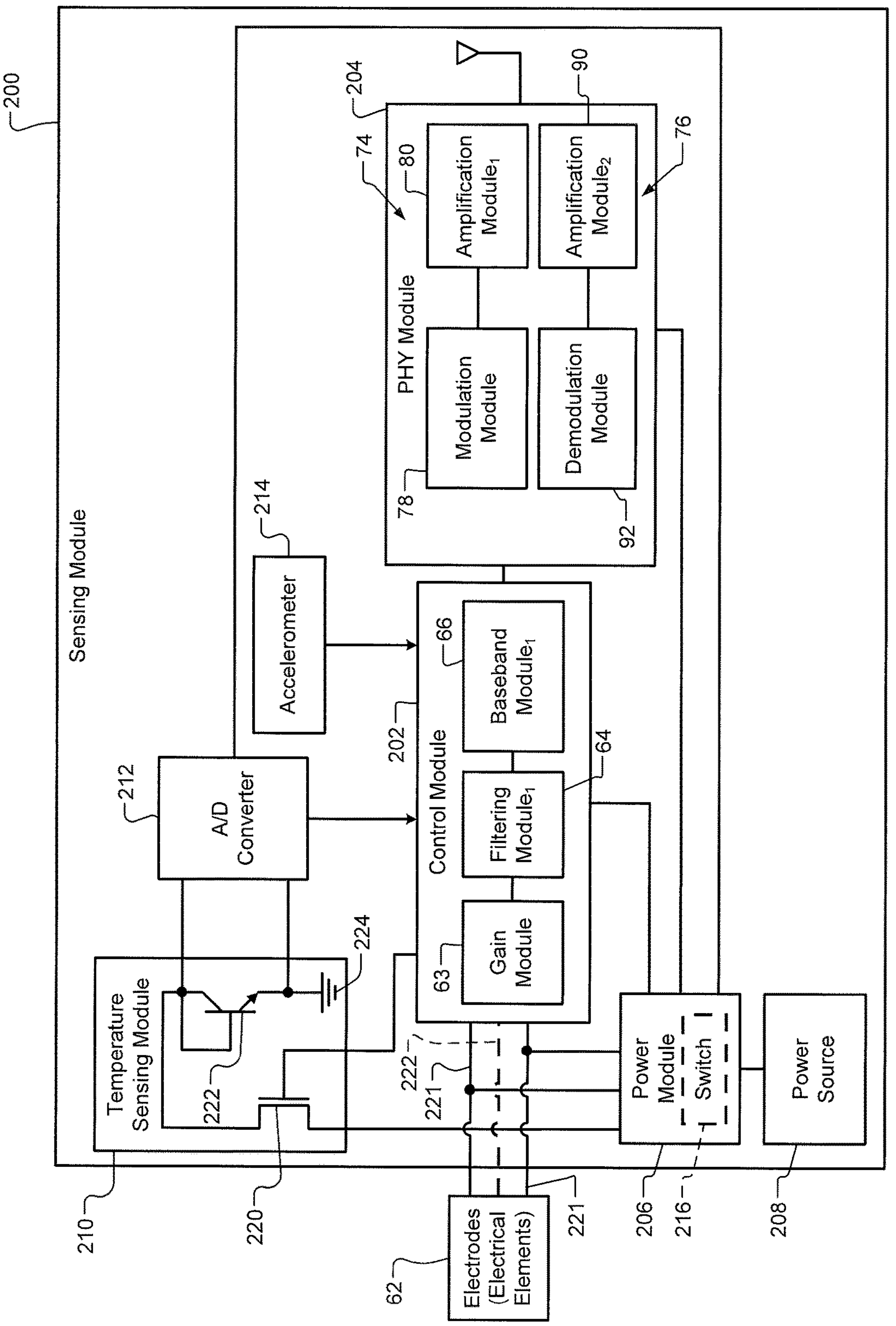
FIG. 4 is a functional block diagram of another sensing module in accordance with the present disclosure.

Referring now to FIG. 1 and FIG. 4, which shows a sensing module 200. The sensing module 200 may be included in any of the sensors disclosed herein. For example, the sensing module may be used on any of the sensors shown in FIGS. 1-4, 7A-13, and 23-34. The sensing module 200 includes the control module 202, a PHY module 204, a power module 206, a power source 208, a temperature sensing module 210, an A/D converter 212, and an accelerometer 214. Although shown separate from the control module 202, the PHY module 204, the power module 206, the temperature sensing module 210 and/or the A/D converter 212 may be included in and as part of the control module 202.

The control module 202 includes the gain module 63, the filtering module 64 and the BB module 66 of FIG. 2. The PHY module 204 includes the modulation module 78, the demodulation module 92 and the amplification modules 80, 90 of FIG. 2.

The control module 202, the PHY module 204, the temperature sensing module 210, and the A/D converter 212 operate based on power from the power module 206. The power module 206 receives power from the power source (e.g., a battery). The power module 206 may include a switch 216 as shown (or a pull-tab) to turn ON and/or OFF the power module 206 and thus turn ON and/or OFF the sensing module 200 and/or the corresponding sensor. The switch 216 may be manually operated or may be operated by the power module 206, the control module 202 and/or the PHY module 204. In one embodiment, the switch 216 is manually operated and at least partially exposed on an exterior of the sensing module 200 and/or corresponding sensor housing. In another embodiment, the switch 216 includes one or more transistors located in the control module 202, the PHY module 204, and/or in the power module 206, as shown. If included in one of the modules 202, 204, 206, the switch 216 is not exposed on an exterior of the sensing module 200 and/or the corresponding sensor housing. The state of the switch 216 may be controlled by the control module 202, the PHY module 204, and/or the power module 206 based on signals received from the electrodes 62, the CIM 52, and/or the NIM device 162 of FIGS. 2-3. Transitioning the switch 216 via one of the modules 202, 204, 206 from a first state to a second state to turn ON at least a portion of the sensor and/or at least a portion of the one or more of the modules 202, 204, 206 may be referred to as an “auto-start”.

The sensing module 200 may operate in: a high power mode (fully powered mode), a low (or idle) power mode (partially powered or transmitting less frequently then when in the high power mode), a sleep mode, or OFF. Operation in and transition between these modes may be controlled by one or more of the modules 202, 204, 206. As an example, the sensor may be OFF (or dormant) while being shipped and/or not in use. The sensor may also be OFF if: not yet communicated with a CIM and/or NIM device; a connection has not yet been established between the sensing module 200 and a CIM and/or NIM device; the sensor has not yet been assigned to a CIM and/or NIM device; and/or the sensor has not yet been assigned one or more time slots in which to communicate with a CIM and/or NIM device.

Transitioning to the low power mode, the sleep mode and/or to OFF decreases power consumption and can aid in minimizing size of the power source 208. While partially powered, the control module 202 and/or portions of the control module 202 and the PHY module 204 may be deactivated. The receiver path of the PHY module 204 may remain activated to (i) receive signals from the CIM 52 and/or portions of the control module 202, and (ii) detect electromyographic signals. The transmit path 74 of the PHY module 204 and/or other portions of the sensor that are not experiencing activity may be deactivated. Transitioning between the stated modes is further described below.

When a surgery is performed, an operating room is generally kept at a low temperature. This in turn can decrease temperature of a patient. Studies have shown that if a patient is kept warm (e.g., within a predetermined range of a predetermined temperature or a normal body temperature, such as 98.6° F.) better outcomes are achieved. To maintain a temperature of a patient, heaters may be used to blow warm air under the patient and/or heat portions of a table on which a patient is lying. The patient may also be covered or wrapped in blankets. If a heater is broken, accidentally disconnected, not setup properly and/or is operating improperly, the temperature of the patient can drop. Unfortunately, there can be a long lag time from when the heaters fail to when a decrease in the temperature of the patient is detected. By the time the decrease in the temperature of the patient is detected by, for example, a surgeon or surgical assistant, the temperature of the patient may have been below the predetermined range for an extended period of time.

To aid in early detection of changes in temperatures of a patient, the sensor includes the temperature sensing module, which may be used to detect a temperature where the sensor is located. This temperature may be based on or represent a temperature of a portion of a patient on which the sensor is attached. While the temperature sensor may not be in direct contact and/or directly indicate a temperature of the portion of the patient, the temperature sensor can provide a temperature signal indicative of an average temperature in a proximate area of the temperature sensor.

Referring again also to FIG. 1, one or more of the sensors 12, 13 may include a temperature sensing module (e.g., the temperature sensing module 210) and/or an accelerometer (e.g., the accelerometer 214). By including temperature sensing modules in sensors, temperatures of various points on a patient may be monitored. This further aids in early detection of changes in temperatures of a patient. The sensors provide an earlier indication of a temperature issue than a sensor used to detect a change in a core body temperature of the patient, as the limbs or exterior of the body tends to decrease in temperature quicker than the core body temperature. The core body temperature may refer to, for example, an internal temperature within a trunk (or chest) of the body.

The temperature sensing module 210 includes a first transistor 220 and a second transistor 222. The first transistor 220 may be transitioned between states to supply current to the second transistor 222. This turns ON the temperature sensing module 210. The second transistor 222 is configured to detect a temperature. As an example, the first transistor 220 may be a metal-oxide-semiconductor field-effect transistor (MOSFET) and includes a drain, a gate and a source. The second transistor 222 may be a bipolar junction transistor (BJT) and includes a collector, a base and an emitter. The transistors 220, 222 are shown for example purposes only, one or more of the transistors 220, 222 may be replaced with other transistors or other similarly operating circuitry. The drain is connected to and receives current from the power module 206. The gate is connected to and receives a control signal from the control module 202. The source of the first transistor 220 is connected to the collector and the base. The collector is connected to a ground terminal 224. The collector and the emitter are also connected to the A/D converter 212.

The second transistor 222 is connected in a diode configuration. Temperature dependence of the base-to-emitter voltage (Vbe) is the basis for temperature measurement. The base-to-emitter voltage Vbe is dependent on temperature while (i) the power source 208 and the power module 206 supply a constant level of current to the collector via the first transistor 220, and (ii) a voltage across the base and the collector is zero. The voltage across the base (or collector) and the emitter is detected by the A/D converter. The detected voltage is converted to a temperature via the control module 202. The control module 202 receives a digital signal from the A/D converter and determines the temperature. The temperature may be determined using, for example, expression 1, where A is a predetermined multiplier constant and B is a predetermined offset constant.

$$A \cdot Vbe + B \quad [1]$$

In addition to detecting electromyographic signals and temperature, the sensing module 200 may also detect other parameters, such as heart rate, respiration rate, and/or muscle spasms. These parameters may be determined via one or more of the control modules 202, 102, 140, 164 of the sensor, the CIM 52 and the NIM devices 54, 162 of FIGS. 2-3. The NIM devices 54, 162 may generate an alert signal and/or display these parameters on the display 146. This information may also be used to provide an early indication that a patient is coming out from anesthesia prematurely. The electrodes 62 may be monitored for EMG purposes as well as for heart rate, respiration rate, and/or muscle spasms purposes. To detect this information, the sensor may be attached to (or mounted on) a trunk of a patient.

A heart rate may be in a same frequency band as an electromyographic signal. A heart rate is periodic unlike an electromyographic signal. A voltage potential detected as a result of a beating heart may have a larger amplitude (or magnitude) than amplitudes (or magnitudes) of an electromyographic signal. A respiration rate is typically in a lower frequency band than an electromyographic signal. A muscle spasm may have a distinguishable frequency and/or distinguishable frequency band. Thus, one or more of the control modules 202, 102, 140, 164 may distinguish between signals or portions of signals corresponding to a heart rate, a respiration rate, and an electromyographic signal based on these differences. If the control module 202 of the sensor detects heart rate, respiration rate, and/or muscle spasms, the control module 202 may wirelessly transmit this information to the CIM 52 and/or one of the NIM devices 54, 162. The NIM devices 54, 162 may then display this information and/or generate an alert signal if one or more of these parameters are outside of respective predetermined ranges and/or thresholds.

In addition to or as an alternative to monitoring the electrodes 62 to detect heart rate, respiration rate, and/or muscle spasms, the sensor includes an accelerometer. As similarly described above, one or more of the control modules 202, 102, 140, 164 may monitor acceleration signals generated by the accelerometer 214 to detect heart rate, respiration rate, and/or muscle spasms. This acceleration signals and/or heart rate, respiration rate, and/or muscle spasm information determined based on the acceleration signals may be wirelessly transmitted from the sensor and/or PHY module 204 to the CIM 52 and/or one of the NIM devices 54, 162.

As is further described below with respect to FIG. 21, the sensor may "self-awake". In other words, the sensor may automatically transition from being OFF or being in the low power (or sleep) mode to being powered ON and being in the high power mode when attached to a patient. For example, while not attached to a patient, there is an "open" circuit between the electrodes 62. Thus, an impedance between the electrodes 62 is high (e.g., greater than 10 kilo-Ohms (kOhms)). Subsequent to attaching the sensor to the patient, an impedance between the electrodes 62 is low (e.g., less than 1 kOhms) and/or significantly less then when the sensor was not attached. This difference in impedance can be detected and cause the power module 206 and/or the control module 202 to switch operating modes.

In another embodiment, the electrodes 62 and the impedance of the patient operate as a switch to activate the power module 206. Upon activation, the power module 206 may supply power to the control module 202 and/or the PHY module 204.

In yet another embodiment, the power module 206 (or analog front end) is configured to generate a DC voltage while the sensor is not attached to a patient. Generation of the DC voltage may be based on the impedance between the electrodes 62. This DC voltage is detected by the control module 202. The control module 202 remains in the low power (or sleep) mode while receiving the DC voltage. The power module 206 ceases to provide the DC voltage when the electrodes are attached to the patient. This causes the control module to transition (i) from being OFF to being in the low power mode or high power mode, or (ii) from being in a sleep mode to being in the low power mode or the high power mode.

The control module 202 and/or the power module 206 may periodically transition between operating in a low power (or sleep) mode and the high power mode to check the impedance between the electrodes 62 and whether the DC voltage is provided. This may occur every predetermined period (e.g., 30-60 seconds). In another embodiment, in response to the electrodes 62 being attached to a patient, the power module 206 may transition (i) from not supplying power to the control module 202, the PHY module 204 and/or portions thereof to (ii) supplying power to the control module 202, the PHY module 204 and/or portions thereof.

Although the modules 204, 206, 210 and the A/D converter 212 are shown as being separate from the control module 202, one or more of the modules 204, 206, 210 and the A/D converter 212 or portions thereof may be incorporated in the control module 202. Also, the electrodes 62 may include two or more electrodes. Signal lines 221 are shown for two of the electrodes. A third signal line 222 may be included for noise feedback cancellation. This is described further with respect to FIGS. 7A-7B.

Referring now to FIGS. 1-3 and FIG. 5, a stimulation probe device 230 is shown, which may be in communication with the CIM 52 and/or one of the NIM devices 54, 162. The stimulation probe device 230 includes a control module 232, a memory 234, a PHY module 236, a stimulating module 238, electrodes 240, a power module 242, and a power source 244. The stimulating module 238 receives power from the power module 242 and generates stimulation signals via the electrodes 240, which are supplied to tissue of a patient. Although the modules 236, 238, 242 are shown as being separate from the control module 232, one or more of the modules 236, 238, 242 or portions thereof may be incorporated in the control module 232. The stimulating module 238 may detect a voltage supplied to the electrodes 240 and/or voltage potentials applied across two of the electrodes 240 and generate stimulation information signals indicating the same. The stimulating module 238 may include a current-to-voltage conversion module 246 for measuring current supplied to one or more of the electrodes 240 and generate a stimulation information signal indicating the same. The stimulation information signals may be provided to the control module 232.

The control module 232 wirelessly communicates with the CIM 52 and/or one or more of the NIM devices 54, 162 via the PHY module 236 and an antenna 248. The control module 232 includes a filtering module 250 and a BB module 252. The filtering module 250 may operate as a bandpass filter and filter out frequencies of the amplified signals outside of a predetermined frequency range and a direct current (DC) voltage. This can eliminate and/or minimize noise, such as 60 Hz noise. The filtering module 250 may receive stimulation information signals from the stimulating module 238 and convert the stimulation information signals and/or signals generated based on the stimulation information signal to BB signals. The stimulating module 238 may monitor and indicate to the control module 232 actual voltages, current levels, amplitudes, and durations of stimulation pulses via the stimulation information signals. The control module 232 may then transmit this information via the PHY module 236 to the CIM 52 and/or one of the NIM device 54, 162.

The BB module 252 may include an analog-to-digital (A/D) converting module 254 and convert the BB signals from the filtering module 250 to digital BB signals. The BB module 252 and/or the A/D converting module 254 may sample the output of the filtering module 250 at a predetermined rate to generate frames, which are included in the digital BB signal. By A/D converting signals at the sensor as opposed to performing an A/D conversion at the CIM 52 or one of the NIM devices 54, 162, opportunities for signal interference is reduced.

The BB module 252 may then upconvert the digital BB signal to an intermediate frequency (IF) signal. The BB module 252 may perform DSSS modulation during upconversion from the digital BB signal to the IF signal. The BB module 252 may include a mixer and oscillator for upconversion purposes. The BB module 252 and/or the control module 232 may compress and/or encrypt BB signals transmitted to the PHY module 236 prior to upconverting to IF signals and/or may decompress and/or decrypt signals received from the PHY module 236.

The BB module 252 may provide a received signal strength indication (RSSI) indicating a measured amount of power present in a received RF signal. This may be used when determining which of multiple CIMs and/or NIM devices to communicate with. The control module 232 may select a CIM and/or a NIM device corresponding to a SYNC request signal and/or a payload request signal having the most power and/or signal strength. This may include selecting a channel on which the SYNC request signal and/or the payload request signal was transmitted and communicating with the CIM or the NIM device on that channel. This allows the control module 232 to select the closest and proper CIM and/or NIM device. This selection may be performed when the stimulation probe device has not previously communicated with a CIM and/or a NIM device and/or has been reset such that the stimulation probe device does not have a record of communicating with a CIM and/or a NIM device.

The memory 234 is accessed by the control module 232 and stores, for example, parameters 260. The parameters 260 may include parameters provided in SYNC request signals and/or parameters associated with stimulation pulses generated via the electrodes 240. The parameters associated with stimulation pulses may include voltages, wavelengths, current levels, amplitudes, peak magnitudes, pulse durations, etc.

The PHY module 236 includes a transmit path 262 (or transmitter) and a receiver path 264 (or receiver). The transmit path 262 includes a modulation module 266 and an amplification module 268. The modulation module 266 modulates the IF signal to upconvert the IF signal to a RF signal. This may include GFSK modulation. The modulation module 266 may include, for example, a filter, a mixer, and an oscillator. The amplification module 268 may include a power amplifier 269, which amplifies the RF signal and transmits the RF signal via the antenna 248.

The receiver path 262 includes a second amplification module 270 and a demodulation module 272. The second amplification module 270 may include a LNA 274. The second amplification module 270 amplifies RF signals received from the CIM. The demodulation module 272 demodulates the amplified RF signals to generate IF signals. The IF signals are provided to the BB module 252, which then downconverts the IF signals to BB signals. The A/D converting module 254 may include a D/A converter to convert the BB signals to analog signals. The RF signals received from the CIM 52 may include, for example, SYNC request signals or portions thereof, as further described below. Examples of information included in the SYNC request signals is shown and described below with respect to Tables 1-4.

The power module 242 receives power from the power source 244 and supplies the power to the stimulating module 238, the control module 232 and the PHY module 236. The power module 242 may include a switch 276. The switch 276 may be actuated to generate stimulation pulses. When the switch 276 is closed or toggled and/or when the control module 232 generates a control signal commanding generation of one or more stimulation pulses, the power module 242 and/or the control module 232 signals the stimulating module 238 to generate the one or more stimulation pulses. The timing, amplitude, and/or duration of each of the stimulation pulses may be based on information received from the CIM 52 and/or one of the NIM devices 54, 162. Frequency of the stimulation pulses and/or time between the stimulation pulses may also be controlled and based on corresponding information received from the CIM 52 and/or one of the NIM devices 54, 162.

Figure 6:
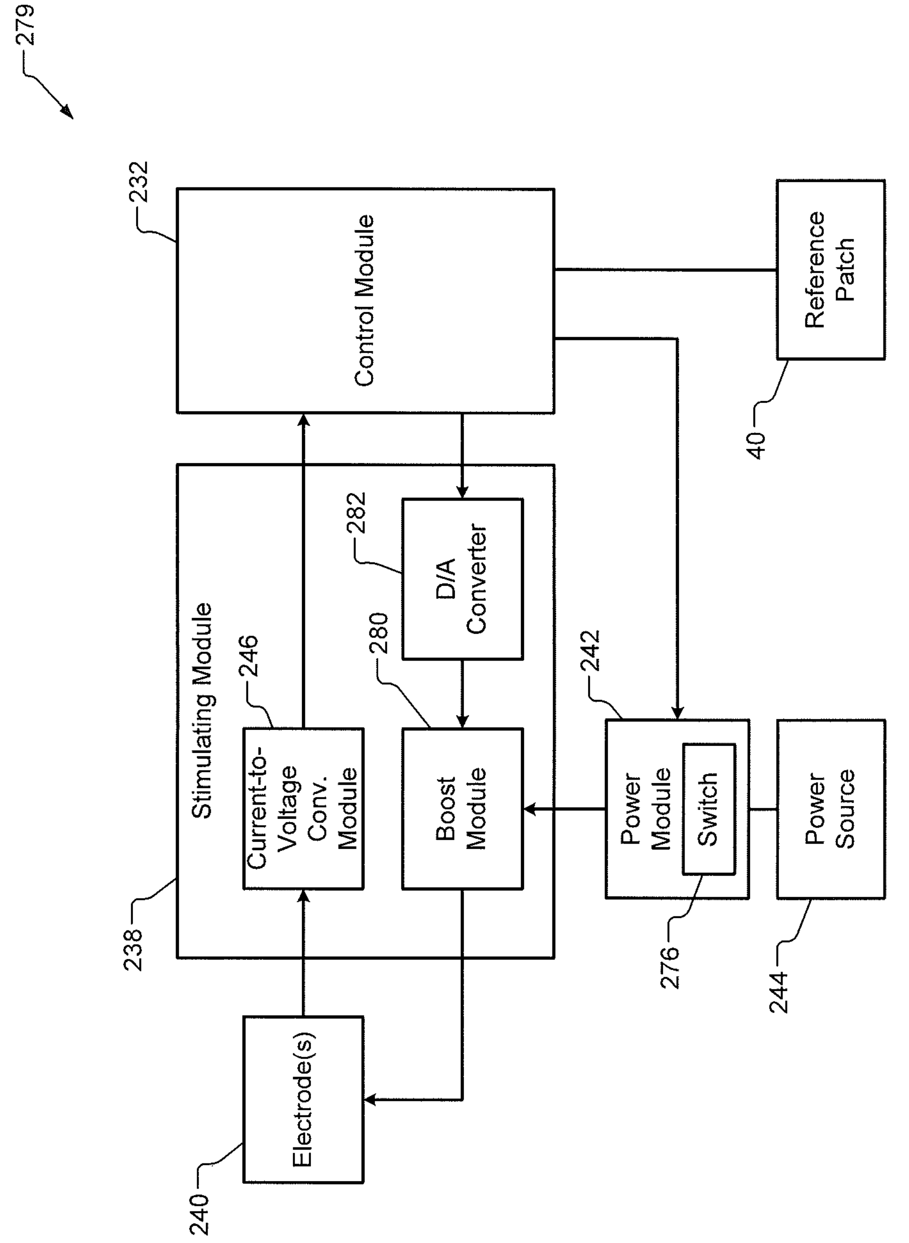
FIG. 6 is a functional block diagram of a portion of the stimulation probe device in accordance with the present disclosure.

Referring also to FIG. 6, which shows a portion 279 of the stimulation probe device 230. The stimulation probe device 230 includes the control module 232, the stimulating module 238, the electrodes 240, the power module 242 with the switch 276, and the power source 244. The control module 232 may be connected to the reference patch 40. In one embodiment, the stimulating module 238 is connected to the reference patch 40. The stimulating module 238 may include the current-to-voltage conversion module 246, a boost module 280, and a D/A converter 282. The current-to-voltage conversion module 246 converts a current supplied to the electrodes 240 to a voltage, which is detected by the control module 232. The control module 232 may include an A/D converter to convert a voltage signal received from the current-to-voltage conversion module 246 to a digital signal.

The D/A converter 282 may convert an analog control signal from the control module 232 to a digital control signal. The digital control signal is provided to the boost module 280 and sets a current level, a voltage, and a duration of one or more stimulation pulses to be generated by the boost module 280 via the electrodes 240. The boost module 280 generates stimulation signals having the stimulation pulses to be supplied to the electrodes 240. The stimulation signals have increase voltage, current and/or power over other signals (e.g., signals transmitted between other modules and/or RF signals) transmitted in the WNIM system 10. The increased voltage, current and/or power generates the stimulation pulses to stimulate tissue (nerve or muscle tissue) of a patient. The boost module 280 receives power from the power module 242. The control module 232 may control the power module 242 to supply a selected amount of current to the boost module 280 for generation of the stimulation signals.

Although not shown, the reference patch 40 may be replaced with and/or configured as a "smart" reference patch that is configured to wirelessly communicate with the stimulation probe device 230. The smart reference patch may, for example, be configured similar to the sensing module 50 of FIGS. 2-3 and may include one or more electrodes, a control module and a PHY module having a transmitter path. The control module and the transmitter path of the reference patch 40 may be configured similar to and operate similar to the control module 56 and the transmit path 74 of the sensing module 50 of FIG. 2 or 3. The control module of the reference patch 40 may be connected to the one or more electrodes and detect and wirelessly transmit a reference voltage at the one or more electrodes to the stimulation probe device 230. The reference voltage may be transmitted via the transmitter path of the reference patch 40. The control module of the reference patch 40 may generate a reference voltage signal that indicates the reference voltage. The reference voltage may be a constant voltage or may vary depending on the state of the patient in an area where the reference patch 40 is attached.

Referring now to FIG. 1 and FIGS. 7A-7B, which show a three-pad sensor 300. The sensor 300 may replace any one of the sensors disclosed herein. The sensor 300, as shown includes a base 302 (may be referred to as a patch) having electrodes 304 and an electronic control module assembly 305. The electronic control module assembly 305 that is modular and includes a control (or sensing) module 306 mounted on a substrate 307, a power source support member 308, a power source 310, and a housing 312. In FIGS. 7B, the base 302 is shown without the electronic control module assembly 305.

The base 302 may include a flexible substrate 314 and an adhesive layer 316 attached to a bottom surface of the substrate 314. The adhesive layer 316 may be attached to, for example, skin of a patient. The control module 306 may include a PHY module (e.g., the PHY module 204 of FIG. 4) and a power module (e.g., the power module 206 of FIG. 4). The control module 306, the PHY module and the power module may operate similar to the control module 202, the PHY module 204 and the power module 206 of FIG. 4 and may wirelessly communicate with the CIM 52 and/or one of the NIM devices 54, 162.

The power source support member 308 may be attached to the substrate 307 and hold the power source 310 to the control module 306. The power support member 308 may be, for example, a clip. The power source 310 may be held between the control module 306 and the power source support member 308. The electronic control module assembly 305 may attach to the top of the electrodes 304 via receiving connectors 317. The receiving connectors 317 may snap on and off of the electrodes 304. This allows the electronic control module assembly 305 to be modular such that the electronic control module assembly 305 may removed from the patch and used on, for example, another patch. The electronic control module assembly 305 may be reusable and the patch 302 may be unreusable. For example, the electronic control module assembly 305 and the patch 302 may be applied to one location on a patient during a first period of time. The electronic control module assembly 305 may then be removed from the patch 302 and snapped onto a different patch, applied to a second location on the patient, for use during a second period of time. As another example, the electronic control module assembly 305 and the patch 302 may be applied to a first patient during a first period of time. The electronic control module assembly 305 may then be removed from the patch 302 and snapped onto a different patch, applied to a second patient, for use during a second period of time.

Although the sensor 300 is shown as having three electrodes 304, the sensor 300 may have two or more electrodes. The electrodes 304 extend upward from the base 302 and connect to electrically conductive pads 318 on the bottom of the adhesive layer 316. The pads 318 may be in contact with skin of a patient when attached to the patient.

The third one of the electrodes 304 may be used as a feedback terminal to supply an inverted common mode noise signal to the patient. The inverted common node noise signal is supplied to the patient to cancel or attenuate a common node nose signal detected on the other two electrodes. The common node nose signal may be detected, for example, at a node between resistors of a voltage divider of the sensor. The control module 306 may: monitor voltage signals at the two electrodes and the node to detect the common node noise signal; invert the common node noise signal; filter the inverted common node noise signal; and feedback the inverted and filtered common node noise signal back to the patient. The control module 306 may feedback the inverted and filtered common node noise signal (referred to as a feedback signal) to cancel low frequency noise. This "cleans up" voltage signals detected at the two electrodes and used to monitor evoked tissue response signals, heart rate, respiration rate, muscle spasms, etc. The feedback signal may be, for example, a 50-60 Hz signal. As an example, the control module may include four amplifiers and the voltage divider. Signals received at each of the other two electrodes may be amplified by respective first and second amplifiers. Outputs of the first and second amplifiers may be provided to respective ends of the voltage divider. Voltages at the ends of the voltage divider may be provided as a differential signal to inputs of the third amplifier. An output of the third amplifier may be wirelessly transmitted to a CIM and/or NIM device. The node may be connected between resistances of the voltage divider. A signal at the node may be amplified via the fourth amplifier and fed back to the third one of the electrodes 304.

The control modules disclosed above may include digital signal processing algorithms that further suppress noise over that provided by the above disclosed filters. The control modules disclosed above may also include algorithms for processing and distinguishing between signals detected via the sensors disclosed herein.

Figure 11:
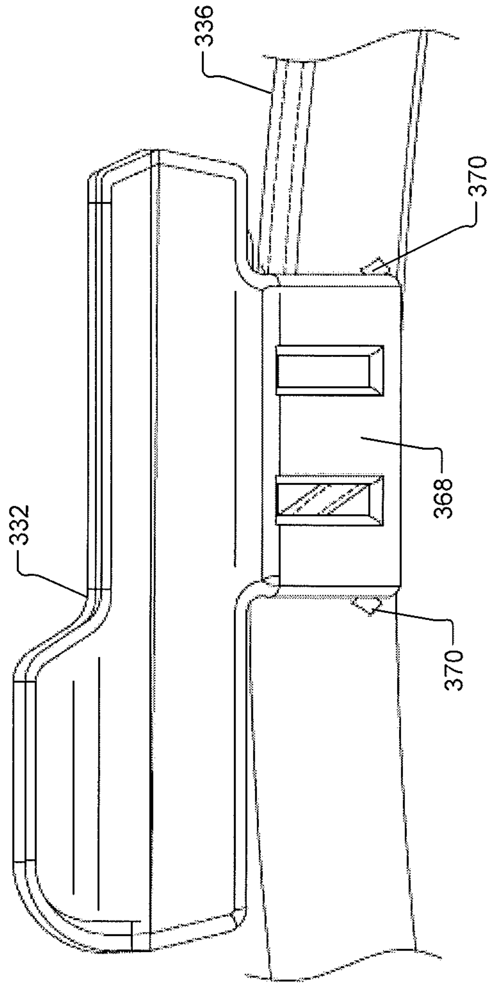
FIG. 11 is a side view of a housing of the EMG endotracheal tube assembly of FIG. 8.
Figure 12:
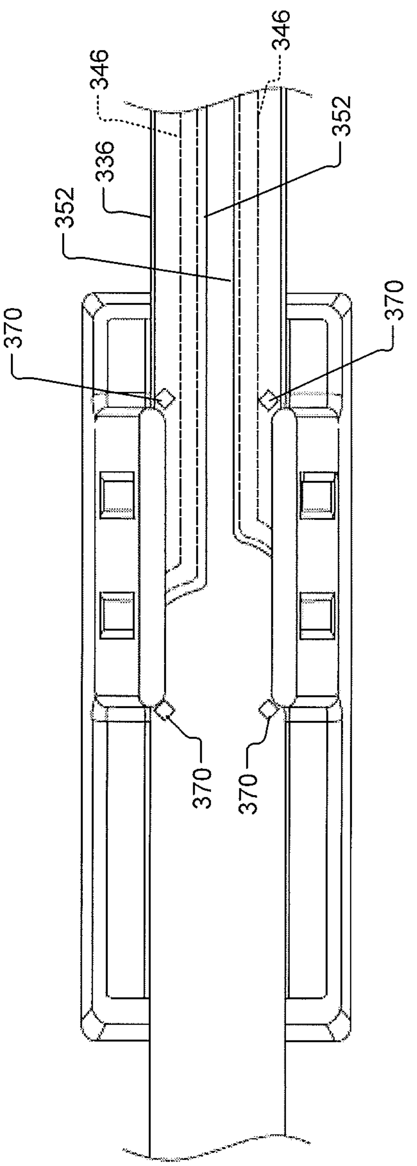
FIG. 12 is a bottom view of the housing of the EMG endotracheal tube assembly of FIG. 8.
Figure 13:
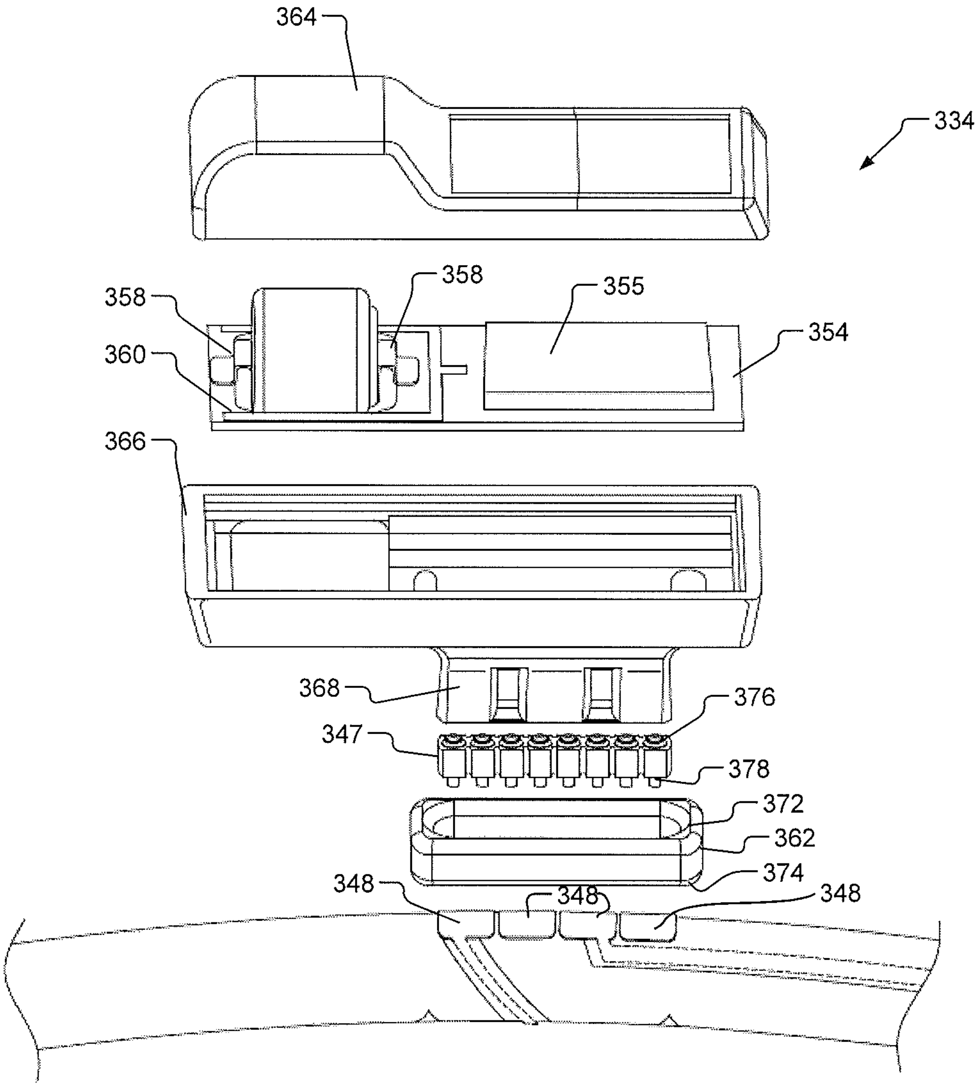
FIG. 13 is an exploded view of the housing and corresponding electronic assembly of the EMG endotracheal tube assembly of FIG. 8.

FIGS. 8-13 show an EMG endotracheal tube assembly 330 and corresponding housing 332. FIGS. 11-13 show the housing 332 and corresponding electronic assembly 334 of the EMG endotracheal tube assembly 330 of FIGS. 8-10. The EMG endotracheal tube assembly 330 includes an EMG tube 336 having a distal (first) end 338 and a proximal (second) end 340. The distal end 338 is connected to a connector 342, which may be connected to a pump for supplying air and/or a fluid to a patient via the EMG tube 336. The EMG tube 336 may be inserted in a throat of a patient and the air and/or fluid may be supplied to, for example, lungs of the patient. The proximal end 340 includes an inflatable portion 344 (shown in an inflated state), which may be used to seal off, for example, a trachea to prevent any other fluid or substance from passing around the inflated portion 344 and entering the lungs.

The EMG endotracheal tube assembly 330 also includes the housing 332 having the electronic assembly 334, electrodes 346, spring loaded pin elements 347, a first set of contacts 348, and a second set of contacts 350. The electronic assembly 334, electrodes 346, spring loaded pin elements 347, and contacts 348, 350 may collectively be referred to as a sensor. The electrodes 346, the contacts 348, and/or the contacts 350 may be painted on the EMG tube 336. In another embodiment, the electrodes 346, the contacts 348, and/or the contacts 350 are printed on the EMG tube and/or are implemented as a portion of a flexible printed circuit board (PCB).

The electrodes 346 may extend from the first set of contacts 348 to the second set of contacts 350. The electrodes 346 extend in parallel along the EMG tube 336 and are separated as to not be in contact with each other. One or more insulation layers 352 may be applied over the electrodes 346 to prevent external electrical contact with the electrodes 346. Each of the insulation layers 352 may cover one or more of the electrodes 346 and may not wrap fully around the EMG tube 336. The first set of contacts 348 are electrically in contact with spring loaded pin elements 347, which are connected to a substrate 354 (or printed circuit board). Each of the electrodes 346, the first set of contacts 348, and the second set of contacts 350 may include conductive ink. The insulation layers 352 may be nonconductive stamps formed of nonconductive material (e.g., rubber).

The sensor may also include the housing 332, the substrate 354, a control module 355, a power source 356, power source support brackets 358, an antenna 360, the spring loaded pin elements 347, and a sealing gasket 362. The housing 332 may include a first upper portion 364, a second lower portion 366, and flanges 368. The housing 332 is formed of a nonconductive material (e.g., plastic). The housing 332 may be shaped to encase the substrate 354, the power source 356, and the control module 355 while minimizing size of the housing 332. The housing 332, via the flanges 368, snaps over the EMG tube 336. The flanges 368 oppose each other and clasp onto the EMG tube 336. The EMG tube 336 may include guide marks 370 for placement and attachment of the housing 332 on the EMG tube 336. The guide marks 370 may be painted on the EMG tube 336 and may be visible underneath the housing 332 and on a side of the EMG tube 336 opposite the housing 332. The EMG tube 336 is pressed between the flanges 368 and against the spring loaded pin elements 347 and the sealing gasket 362. The first portion 364 and the second portion 366 may be sealed to each other via an adhesive, such as an ultraviolet (UV) light cured adhesive. The first portion 364 may be ultrasonically welded to the second portion 366.

The sealing gasket 362 may be adhesively attached to both the second portion of the housing 332 and the EMG tube 336. The sealing gasket 362 is disposed between the second portion 366 of the housing 332 and the EMG tube 336. The sealing gasket 362 may have adhesive layers (or adhesive) on a first side 372 facing the second portion 366 of the housing 332 and on a second side 374 facing the EMG tube 336. The adhesive may be an UV light cured adhesive. The sealing gasket 362 maybe ultrasonically welded to the second portion 366 and/or the EMG tube 336. The sealing gasket 362 provides a fluid tight seal to prevent contaminants from coming in contact with the first set of contacts 348 and/or the spring loaded pin elements 347.

The spring loaded pin elements 347 include respective spring members 376 and pins 378. The spring loaded pin elements 347 are disposed in the sealing gasket 362 and between the substrate 354 and the first set of contacts 348. The pins 378 are spring loaded to maintain contact with the first set of contacts 348. Each of the spring members 376 and/or the pins 378 is in direct or indirect contact with the control module 355. These connections between the spring member 376 and the control module 355 may be provided by, for example, by vias and/or traces in the substrate 354. The sensor may include any number of the spring loaded pin elements 347 and corresponding contacts. More than one spring loaded pin element may be provided for each of the first set of contacts 348.

The power source 356 is disposed on the substrate 354 and is held by the power source support brackets 358, which are connected to the substrate 354. The antenna 360 may be a trace printed and/or disposed on the substrate 354 and is connected to the control module 355. The control module 355 may be configured similarly as and operate similar to any one of the control modules of the sensors disclosed herein. The control module 355, as shown has two channels. Each of the channels is connected to a respective pair of the first set of contacts 348. The dual channels may be provided for redundancy reasons to assure that signals provided at the second set of contacts 350 are detected by the control module 355. The second channel may be used to backup the first channel. As disclosed below, each of these channels may be assigned a respective one or more time slots in communicating with a CIM and/or a NIM device.

FIG. 14 shows a plot of a stimulation pulse 390 and a corresponding evoked response signal 392. The stimulation pulse 390 may be generated by, for example, one of the stimulation probe devices (e.g., the stimulation probe device 230 of FIG. 5) disclosed herein. The evoked response signal 392 may represent nerve and/or muscle activity detected by one of the sensors disclosed herein.

Stimulation is a feature provided for nerve and/or muscle monitoring. The reaction time between stimulation and muscle response is used for both nerve location sensing and nerve health monitoring. This can be achieved by measuring time between stimulation and reaction (e.g., time between a stimulation pulse and an evoked response). The wireless RF protocol disclosed herein may include determining amounts of time between stimulation and evoked responses. The time between stimulation and evoked responses may be determined by the NIM devices disclosed herein.

Referring now to FIGS. 1-13, the CIMs (e.g., the CIM 52), NIM devices (e.g., the NIM devise 54, 162), sensors (e.g., the sensors 12, 13 and/or the sensors of the embodiments of FIGS. 7A-13), stimulation probe devices (e.g., the stimulation probe devices 14, 230), and reference patches (e.g., the smart reference patch described above) disclosed herein communicate with each other via a wireless protocol disclosed herein. The wireless protocol is designed for wireless transfer of high-rate data from multiple sensors (may be referred to as remote body sensors), stimulation probe devices and/or reference patches to the CIMs and/or the NIM devices. The sensors, stimulation probe devices and reference patches digitize signals and send the signals over-the-air (OTA) when requested by the CIMs and/or the NIM devices. Digitized data is received by the CIMs and/or NIM devices and may be converted to analog data and/or displayed at the NIM devices.

The wireless protocol is designed for handling large amounts of data received at one or more high-data rates (e.g., 2.5 kHz, 5 kHz, or 10 kHz). The sensors, stimulation probe devices and reference patches may be transmitting at a same speed or may be transmitting at different speeds. The sensors, stimulation probe devices and reference patches may each transmit data on one or more channels. Each of the channels may have a same corresponding data rate or may have different corresponding data rates. To transmit and handle multiple channels from multiple devices at the same or different transmission speeds, the wireless protocol includes sensor and stim probe synchronization protocols and low power consumption protocols, some of which have been described above whiles others are described below. The wireless protocol allows for different types of sensors (having different transmit speeds, number of channels, etc.) and different types of stimulation probe devices (having different transmit speeds, number of channels, etc.) to be connected up to the CIMs and the NIM devices. This allows for modular upgrades (e.g., replacement of sensors and/or stimulation probe devices with increase transmission speeds and/or number of channels).

The wireless protocol starts with a payload request, which is generated by a NIM device. The payload request is transferred to a CIM and/or is converted to a SYNC request. The SYNC request is a payload request and is provided as a SYNC signal. The CIM or NIM device may search for a clear channel (channel hop) and select a channel that is not used and has a minimum amount of noise. The selected channel may then be used as a broadcast channel to transmit the SYNC request to sensors and stimulation probe devices in the corresponding WNIM system. The CIM may update the SYNC request and periodically transmit the updated SYNC request. As an example, the CIM may wait a predetermined amount of time (referred to as a predetermined interval) between each transmission of the SYNC signal. The predetermined interval may be, for example, 4 milliseconds (ms).

As a result, SYNC signals may be transmitted every predetermined interval or 4 ms on a selected RF channel. The RF channel may be within a predetermined frequency range (e.g., 2.4-2.484 GHz). Any of the sensors and/or stimulation probe devices within range and that are 'listening' on the broadcast channel is able to receive and interpret the SYNC requests. The payload request and SYNC request may include a predetermined number of words (e.g. 16), where each of the words has 16-bits of information. Examples of content included in the SYNC request and the corresponding words are shown in the below provided tables 1-4.

In the following sections and else where, NIM devices, CIMs, sensors, and stimulation probe devices are described as communicating with each other and transmitting various signals and requests between each other. Each of these transmissions may be generated and/or transmitted by respective control modules and PHY modules of these devices, as described above.

Table 1 shows an example of a payload of a SYNC request. The SYNC request includes 16 words, identified as words 0-15. Word 0 is a CIM or NIM device status word, the content of which is shown in table 2. Words 1 and 11-12 are unused. Word 2 is a stimulation probe device status word, the content of which is shown in Table 4. Words 3-10 are slot status words. An example of the content of each of the slot status words is shown in Table 3. Words 13-15 are stimulation information words. Word 13 indicates a delay period that indicates a period between when a NIM device generates a payload request and a time when the NIM device or a CIM transmits a next SYNC request. A stimulation probe device may adjust timing of data (or a data payload) transmitted from the stimulation probe device based on the delay period. Word 14 indicates a stimulation pulse amplitude. Word 15 indicates a stimulation pulse width (or duration). A stimulation probe device may generate a stimulation pulse based on the words 13-15. Although a certain number of each of the stimulation probe device status word, slot status words, and stimulation information words are shown, the payload of the SYNC request may include any number of each of these words. For example, if more than one stimulation probe device is used, additional stimulation probe device status words and/or stimulation information words may be included. Similarly, if more than 8 channels and/or more than 8 sensors are communicating with the CIM and/or NIM device, then additional slot status words may be included.

TABLE 1

SYNC Request Signal

| Word | SYNC Request |
|---|---|
| 0 | Console Interface Module or NIM Device Status |
| 1 | Spare |
| 2 | Stimulation Probe Device Status |
| 3 | Slot 1 Status |
| 4 | Slot 2 Status |
| 5 | Slot 3 Status |
| 6 | Slot 4 Status |
| 7 | Slot 5 Status |
| 8 | Slot 6 Status |
| 9 | Slot 7 Status |
| 10 | Slot 8 Status |
| 11 | Spare |
| 12 | Spare |
| 13 | STIM Delay |
| 14 | STIM Amplitude |
| 15 | STIM Duration and/or Pulse Width |

The CIM or NIM device status word shown in Table 2 includes 16 global bits identified as bits 0-15. As these are global bits, all of the sensors and/or stimulation probe devices communicating with the CIM and/or NIM device may communicate according to these bits unless otherwise indicated in a corresponding one or more of the slot status words or the stimulation probe device status word. Bits 0-7 (7:0) provide a CIM unique identifier (or NIM device unique identifier). The unique identifier may be used by sensors and/or stimulation probe devices to identify a CIM and/or a NIM device when selecting a channel of a CIM and/or a NIM device. This may assure that a sensor and/or a stimulation probe device communicate with the same CIM and/or NIM device that the sensor and/or stimulation probe device previously communicated with.

Bits 9:8 of the CIM or NIM device status word are request sequencer bits used to indicate which interval sensors and/or stimulation devices are to communicate in. For example, sensors and stimulation probe devices may communicate in respective slots of each interval or may communicate in slots of different intervals. The sensors and/or the stimulation probe device may communicate in one or more of a series of intervals based on these bits. This is further described below with respect to FIGS. 15-17.

Bits 11:10 of the CIM or NIM device status word indicate a speed (i.e. data rate) at which the sensors and/or the stimulation probe devices are to transmit information and/or data to the CIM and/or the NIM device. In the example shown, the data rate may be 0, 2.5 kHz, 5 kHz, 10 kHz depending on the values of the bits 11:10. The data rate may be set less than or equal to a maximum data rate of one or more of the sensors and/or stimulation probe device. In one embodiment, the data rate of bits 11:10 of the CIM or NIM device status word may be set to the lowest maximum data rate of the sensors to accommodate all of the sensors and/or stimulation probe devices.

In another embodiment, the data rate of the bits 11:10 of the CIM or NIM device status word are set to a highest maximum data rate of the sensors. Data rates provided in the slot status words and stimulation probe device status word are used to accommodate sensors and/or stimulation probe devices that are unable to communicate at the highest maximum data rate. The data rate of bits 11:10 of the CIM or NIM device status word may be reduced when a stimulation probe device is OFF, in a sleep mode, and/or is in a low power mode. This reduces power consumption of the sensors and/or stimulation probe devices when data is not being collected and/or monitored as a result of stimulation pulses.

Bits 14:12 are unused. Bit 15 indicates whether the stimulation probe device should be ON to generate a stimulation probe signal. If bit 15 is OFF (or low), then the stimulation probe device may be OFF or in the corresponding low power mode. The sensors and/or the stimulation probe devices may transition between OFF, sleep, low power and/or high power modes based on bits 15 and 11:10. For example, sensors may be in a high power mode when bits 11:10 indicate a first data rate and may be in a low power mode when the bits 11:10 indicate a second data rate, where the second data rate is less than the first data rate.

TABLE 2

| Console Interface Module or NIM Device Status Word | |
|---|---|
| Bit 15 | STIM ON/OFF |
| Bits 14:12 | Spare |
| Bits 11:10 | Frequency (e.g., Bits 00 - 10 kHz, Bits 01 - 5 kHz, Bits 10 - 2.5 kHz, Bits 00 - 0 kHz) |
| Bits 9:8 | Request Sequencer Bits Indicating which of up to Predetermined Number of SYNC intervals (e.g., up to 4 SYNC intervals) |
| Bits 7:0 | Console Unique Identifier (CUID) |

The slot status word shown in Table 3 includes 16 bits identified as bits 0-15. These bits may be referred to as local bits as these bits pertain to a sensor assigned to this slot. Bits 7:0 indicate whether the corresponding time slot (referred to as "the slot") is paired or unpaired. If paired, the slot is assigned to a sensor and bits 7:0 indicate a unique identifier (SUID) of the sensor. If unpaired, the slot is not assigned to a sensor and bits 7:0 indicate a pipe address that a sensor is to communicate to when communicating with the CIM or NIM device. Bits 9:8 indicate whether the corresponding slot is available, in process of being assigned, or is assigned. Sensors may review these bits when determining whether to select this slot. Bits 11:10 indicate a speed at which the sensor assigned to this slot is to transmit information and/or data to the CIM and/or the NIM device. Bits 13:12 indicate a type of the sensor assigned to the slot. Bit 14 is unused. Bit 15 indicates whether a stimulation probe device corresponding to the sensor assigned to the slot is ON. The sensor assigned to the slot may transition between OFF, sleep, low power, and/or high power modes based on bit 15 and/or bits 11:10. As an example, the sensor may be OFF or in the sleep mode and/or low power mode when bits 11:10 indicate a data rate of zero.

TABLE 3

| Slot Status Word | |
|---|---|
| Bit 15 | STIM ON/OFF |
| Bit 14 | Spare |
| Bits 13:12 | Sensor Type - Indicating Number of channels, Speed per channel, and/or Number of Time Slots per SYNC interval |
| Bits 11:10 | Frequency (e.g., Bits 00 - 10 kHz, Bits 01 - 5 kHz, Bits 10 - 2.5 kHz, and Bits 00 - 0 kHz) |

TABLE 3-continued

| Slot Status Word | |
|---|---|
| Bits 9:8 | Slot Status: Bits 00 - Available/Open, Bits 01 - Busy/Sensor Currently Joining, and Bits 10 - Assigned |
| Bits 7:0 | Paired (SUID) or Unpaired (Pipe Address of PHY Module of Console Interface Module or NIM device) |

The slot status word shown in Table 4 includes 16 bits identified as bits 0-15. These bits may be referred to as local bits as these bits pertain to a stimulation probe device assigned to this slot. Bits 0:7 indicate whether the corresponding time slot (referred to as "the slot") is paired or unpaired. If paired, the slot is assigned to a stimulation probe device and bits 0:7 indicate a unique identifier (STIMUID) of the stimulation probe device. If unpaired, the slot is not assigned to a stimulation probe device and bits 0:7 indicate a pipe address that a stimulation probe device is to communicate to when communicating with the CIM or NIM device. Bits 9:8 indicate whether the corresponding slot is available, in process of being assigned, or is assigned. A stimulation probe device may review these bits when determining whether to select this slot. Bits 10:11 indicate a speed at which the stimulation probe device assigned to this slot is to transmit information and/or data to the CIM and/or the NIM device. Bits 13:12 indicate a type of the stimulation probe device assigned to the slot. Bit 14 is unused. Bit 15 indicates whether the stimulation probe device assigned to the slot is ON. The stimulation probe device assigned to the slot may transition between OFF, sleep, low power, and/or high power modes based on bit 15 and/or bits 11:10. As an example, the stimulation probe device may be OFF or in the sleep mode and/or low power mode when bits 11:10 indicate a data rate of zero.

TABLE 4

| Stimulation Probe Status Word | |
|---|---|
| Bit 15 | STIM ON/OFF |
| Bit 14:12 | Spare |
| Bits 11:10 | Frequency (e.g., Bits 00 - 10 kHz, Bits 01 - 5 kHz, Bits 10 - 2.5 kHz, and Bits 00 - 0 kHz) |
| Bits 9:8 | Slot Status: Bits 00 - Available/Open, Bits 01 - Busy/Sensor Currently Joining, and Bits 10 - Used |
| Bits 7:0 | Paired (STIMUID) or Unpaired (Pipe Address of PHY Module of Console Interface Module and/or NIM device) |

Sensors and stimulation probe devices, when joining a WNIM network, may hop frequency (or broadcast) channels to detect SYNC requests. A WNIM network may include one or more sensors, one or more stimulation probe devices, a CIM and/or a NIM device. The sensors and stimulation probe devices may select the channel with the strongest SYNC request at which point the sensors and stimulation probe devices review slot status words and stimulation probe device status words in the SYNC request. The sensors and the stimulation probe devices then select respective available time slots over which to communicate with a CIM and/or NIM device.

Figure 15:
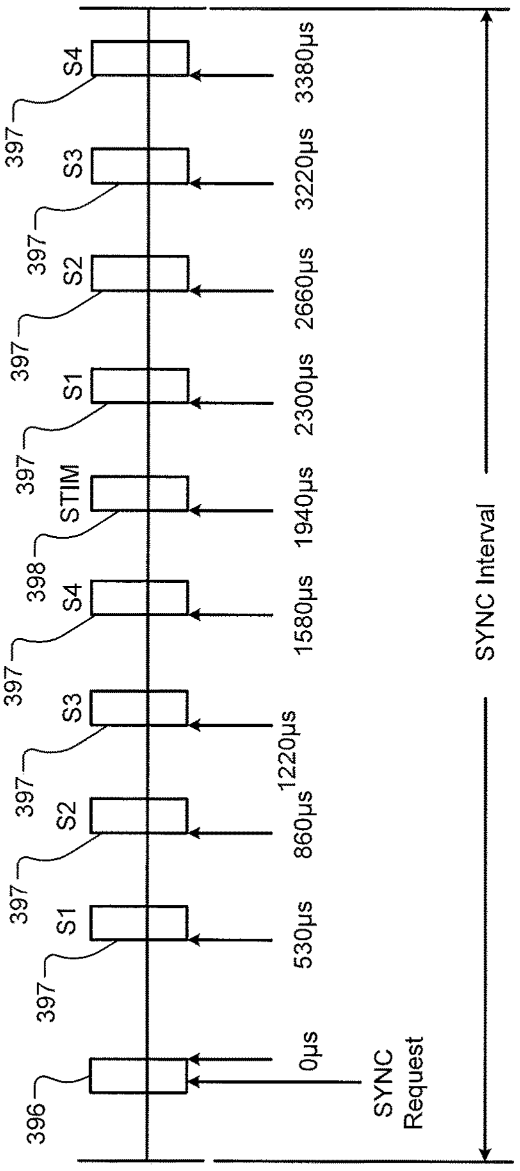
FIG. 15 is a timing diagram illustrating a periodic synchronization (SYNC) interval with two time slots per sensor in accordance with the present disclosure.

To select an available time slot, a sensor or stimulation probe device transmits a data payload during the selected time slot. An example periodic SYNC interval is shown in FIG. 15. The periodic SYNC interval includes a time slot 396 in which a SYNC request is transmitted, eight sensor time slots 397, and a stimulation probe device time slot 398. The periodic SYNC interval is setup for two time slots per each of sensors S1-S4. As such, each of the sensors S1-S4 has one or more unique (or designated) time slots to transmit a data payload in response to the SYNC request. The periodic SYNC interval has a predetermined length (e.g., 4 ms). The predetermined length is the time between consecutive SYNC requests. The periodic SYNC interval may be referred to as a “RF frame”.

The periodic SYNC interval of FIG. 15 may support, for example, four 10 kHz sensors and a stimulation probe device. Each of the four sensors sends data payloads during their designated time slots. Each of the data payloads may include a corresponding SUID and a predetermined number (e.g., 15) of words of data. The data from the sensors may include information disclosed above, such as voltage potentials, current levels, amplitudes, peak voltages (or magnitudes), etc. The data from the stimulation probe device may include information disclosed above, such as amplitude and duration of stimulation pulses. The synchronized timing in respective time slots of the data payloads prevents data payload response signals from being transmitted during a same period and colliding with each other.

Figure 16:
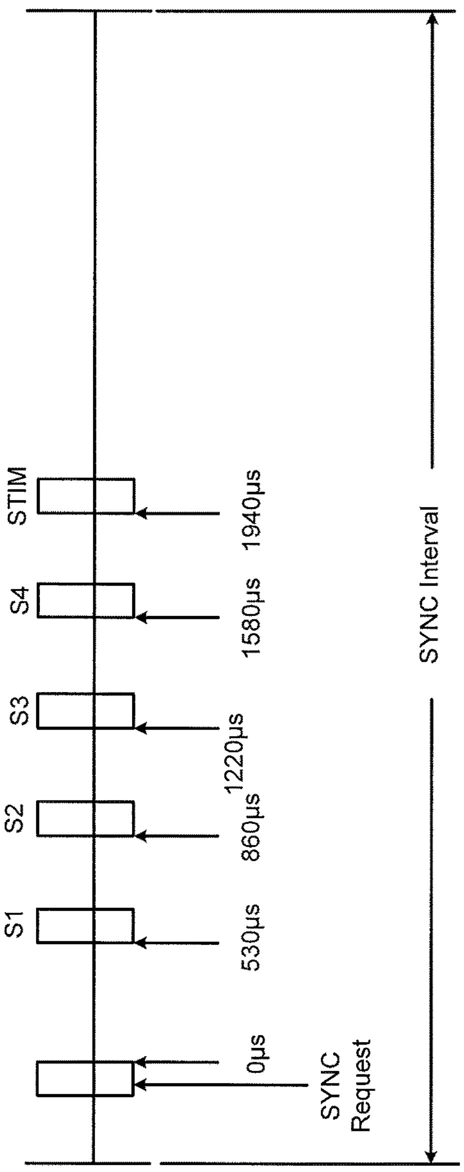
FIG. 16 is a timing diagram illustrating a periodic SYNC interval with a single time slot per sensor in accordance with the present disclosure.
Figure 17:
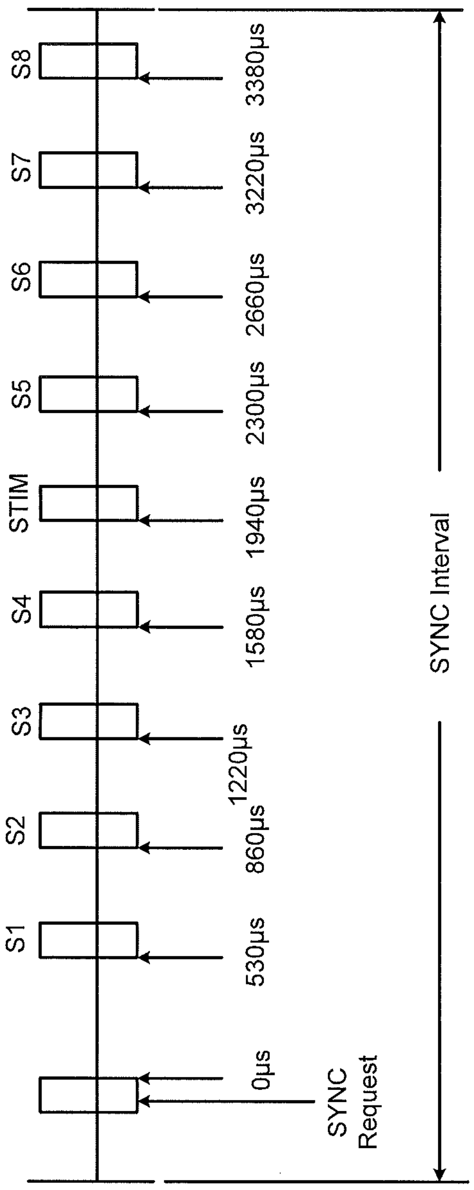
FIG. 17 is a timing diagram illustrating a periodic SYNC interval with a single slot per sensor and an increased number of sensor slots per frame in accordance with the present disclosure.

FIG. 16 provides another example of a periodic SYNC interval setup for a single time slot per sensor and stimulation probe device. In this example, the data rates of the sensors and the stimulation probe device for the example of FIG. 16 may be half the speed of the sensors and stimulation probe device for the example of FIG. 15. For example, the sensors and the stimulation probe device for the example of FIG. 16 may each have an output data rate of 5 kHz. FIG. 17 provides yet another example of periodic SYNC interval setup for eight sensors S1-S8. As an example, each of the sensors S1-S8 may have a single respective time slot and the output data rates of each of the sensors may be 5 kHz.

Although in FIGS. 15-17 a certain number of sensor time slots and stimulation probe time slots are shown per periodic SYNC interval, different numbers of sensor time slots and stimulation probe time slots may be included in a periodic SYNC interval. Also, although the sensors and stimulation probe devices described with respect to each of FIGS. 15-17 have a same output data rate (e.g., 10 kHz or 5 kHz), the sensors and/or stimulation probe devices associated with one or more periodic SYNC intervals may have different output data rates. These different data rates may be indicated in the slot status words and stimulation probe status words of SYNC requests. In addition, each sensor and/or stimulation probe device of a periodic SYNC interval may be designated to a different number of time slots in that periodic SYNC interval than another sensor and/or stimulation probe device.

The time slots of a periodic SYNC interval that are designated to a single sensor or stimulation probe device may all be associated with a single channel of the sensor or stimulation probe device. As another example, one or more time slots of a periodic SYNC interval that are designated to a single sensor or stimulation probe device may be associated with each channel of the sensor or stimulation probe device. In other words, each channel may correspond to respective sets of time slots, where each set has one or more time slots. As another example, a sensor and/or stimulation probe device may select and/or be designated to the same or different time slots of consecutive SYNC intervals.

Figure 18:
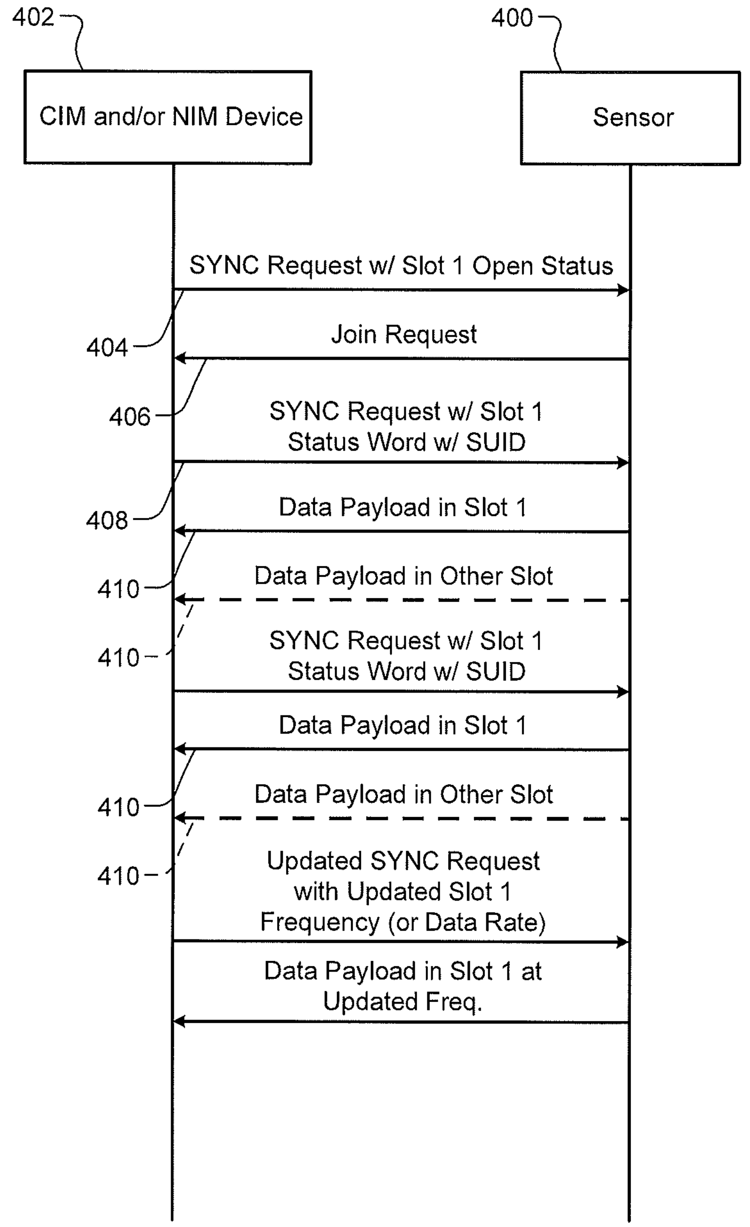
FIG. 18 is a signal flow diagram illustrating a sensor joining and communicating in a WNIM system in accordance with the present disclosure.

Additional details of the wireless protocol are described below with respect to FIGS. 18 and 19. FIG. 18 shows a signal flow diagram illustrating a sensor 400 joining a WNIM network and communicating in a WNIM system with a CIM and/or a NIM device (collectively designated 402). The sensor 400 may refer to any sensor disclosed herein. Similarly, the CIM and/or NIM device 402 may refer to any CIM and/or NIM device disclosed herein. Before a sensor responds to a SYNC request with a data payload, a joining process is performed. Joining establishes a link between the sensor and a CIM and/or NIM device and together the sensor and the CIM and/or NIM device (and/or other sensors and/or stimulation probe devices linked to the CIM and/or NIM device) provide a WNIM network. FIG. 18 shows an example sequence of events performed for the sensor 400 to join the WNIM network and also how different modes of operation are obtained.

A SYNC request signal 404 is transmitted from the CIM and/or NIM device 402 and includes a word for each time slot in a corresponding SYNC interval and is periodically and/or continuously updated and transmitted to indicate the statuses of the slots. To join the WNIM network, the sensor 400 checks all the available slots and selects the time slot in which to transmit a data payload signal to the CIM and/or NIM device 402. Prior to transmitting the data payload, the sensor 400 sends a join request 406 to join the WNIM network and communicate in the selected time slot. The join request 406 may be transmitted in the selected time slot and indicates a SUID of the sensor, the selected time slot, the type of the sensor, a minimum data rate, and/or a maximum data rate of the sensor. In one embodiment, the sensor 400 sends the SUID in the selected time slot and the CIM and/or NIM device 402 has a record of the type and data rates of the sensor.

Based on the join request 406, the CIM and/or NIM device 402 fills an appropriate slot status word with the SUID from the sensor 400. The CIM and/or NIM device 402 may then send an updated SYNC request 408 with the updated slot status word indicating designation of the selected time slot to the sensor 400. The sensor 400 receives the updated SYNC request with the SUID in the corresponding slot status word and responds by sending a data payload to the CIM and/or the NIM device 402 in the selected slot. If more than one slot is selected and/or designated to the sensor 400, the sensor 400 may transmit one or more data payloads 410 in the slots selected and/or designated to the sensor 400. The time slots may be associated with one or more channels of the sensor 400. The transmission of the SYNC requests and the data payloads may be periodically transmitted over a series of periodic SYNC intervals (or RF frames).

Once linked to the CIM and/or NIM device 402, the sensor 400 may now be controlled by the CIM and/or NIM device 402 via transmission of updated SYNC requests. The CIM and/or NIM device 402 may control, for example, output data rates and transitions between power modes of the sensor 400. As an example, the CIM and/or NIM device 402 may update the output data rate from 10 kHz to 5 kHz for the time slot of the sensor 400 by transmitting an updated SYNC request 412. Sensors linked to the CIM and/or NIM device 402 inspect control bits (e.g., bits of the slot status words) in SYNC requests to determine respective operating and/or power modes. The sensors then transition to the indicated operating and/or power modes.

Figure 19:
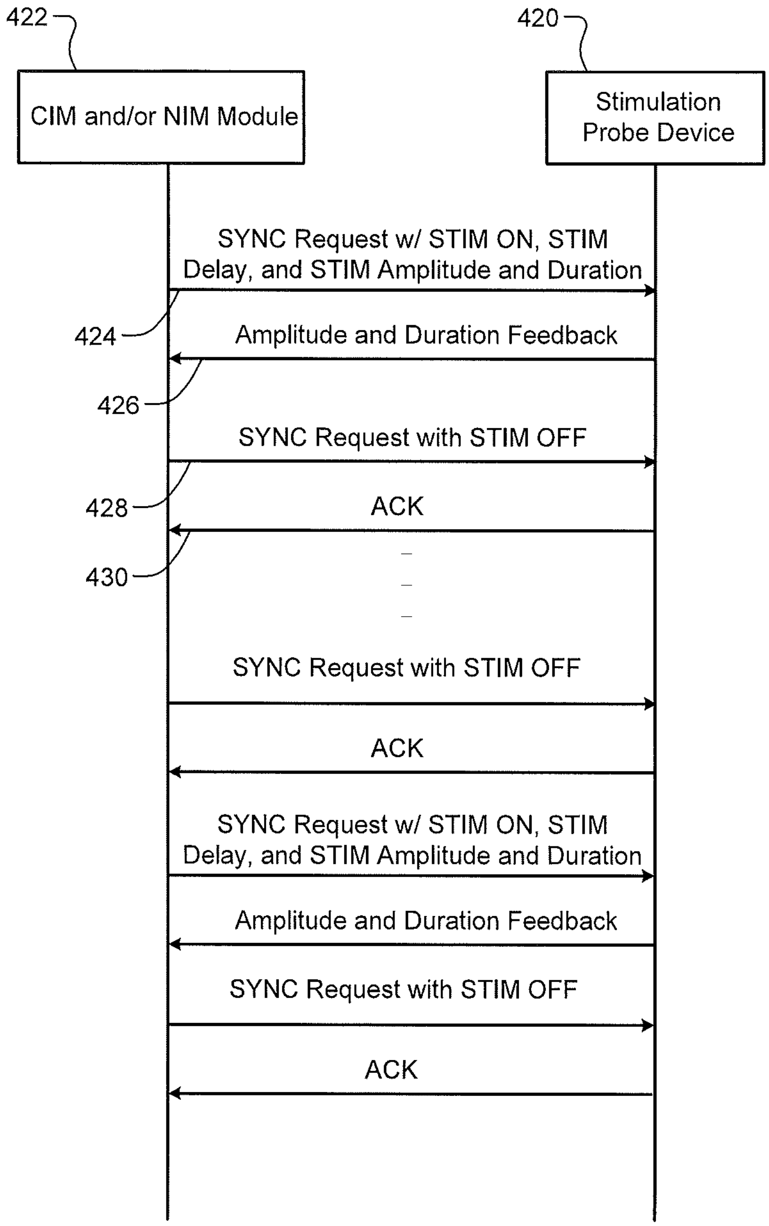
FIG. 19 is a signal flow diagram illustrating a stimulation device joining and communicating in a WNIM system in accordance with the present disclosure.

FIG. 19 shows a signal flow diagram illustrating a stimulation probe device 420 joining a WNIM network and communicating in a WNIM system to a CIM and/or NIM device (collectively designated 422). The stimulation probe device 420 may refer to any stimulation probe device disclosed herein. The CIM and/or NIM device 422 may refer to any CIM and/or NIM device disclosed herein. Generation of stimulation pulses may be initiated at the NIM device and/or CIM 422. The NIM device may issue a payload request with bits 15 of status words indicating generation of a stimulation pulse. The status words may include: a CIM and/or NIM status word; slot status words; and stimulation probe status word. Based on the payload request, the CIM may generate a SYNC request 424 also having bits 15 of status words set to ON to indicate generation of a stimulation pulse. Both the payload request and the SYNC request may indicate a delay, an amplitude of the stimulation pulse, and/or a duration of the stimulation pulse via corresponding words 13-15. In response to bits 15 indicating a stimulation pulse is to be generated, one or more sensors corresponding to the stimulation pulse device 420 and/or being used to monitor the stimulation pulse to be generated may transition to the HIGH power mode. Upon transitioning to the HIGH power mode, the sensors may generate and transmit data payloads at predetermined default frequencies and/or at frequencies indicated by bits 11:10 of the status words of the SYNC request.

In response to the SYNC request 424, the stimulation probe device 420 generates a stimulation pulse, which is provided to a patient. To achieve an accurate timing and measurement of the stimulation pulse in relationship to an evoked response, the delay period provided in the SYNC request 424 is monitored by the stimulation probe device 420. The stimulation probe device 420 generates a response signal 426 indicating the amplitude and duration of the stimulation pulse as applied to the patient.

Subsequent to the response signal 426 from the stimulation pulse device 420, the NIM device and/or CIM 422 generates a payload request (or SYNC request) 428 with the stimulation bits 15 low (or OFF). In response to the received payload request (or SYNC request) the stimulation probe device 420 sends an acknowledgement (ACK) signal 430 to the CIM and/or NIM device 422. Generation of payload request (or SYNC requests) and ACK signals may be repeated until a next stimulation pulse is to be generated in which case the stimulation process may be repeated.

As described above, the CIMs, NIM devices, sensors, reference patches, and stimulation probe devices disclosed herein may communicate with each other using bits within payload requests, SYNCH requests, data payloads, and response signals. The CIMs and/or NIM devices may initiate communication by a sending a payload request (SYNC request). The data payload may include one 16-bit word for payload validation. The 16 bit-word may include a SUID or a STIMUID. When the CIM and/or NIM device receives a data payload, the CIM and/or NIM device compares the SUID or the STIMUID with an expected SUID or STIMUID stored in memory of the CIM and/or NIM device. The SUID or STIMUID may have been stored in the memory when the sensor or stimulation probe device joined the corresponding WNIM network. If the comparison indicates a match, the data in the data payload may be displayed at the NIM device.

Likewise, when the sensor receives the SYNC request, the sensor compares the CUID of the CIM and/or NIM device provided in the SYNC request with an expected CUID stored in a memory of the sensor. The CUID may have been stored in the memory when the sensor joined the corresponding WNIM network. If the comparison of the CUIDs indicates a match, the sensor may respond, depending on mode status bits within a slot status word of the SYNC request, with one or more data payloads in the appropriate time slots following the SYNC request. The mode status bits may be the bits of the slot status word indicating a data rate and/or whether a stimulation pulse is to be generated.

Figure 20:
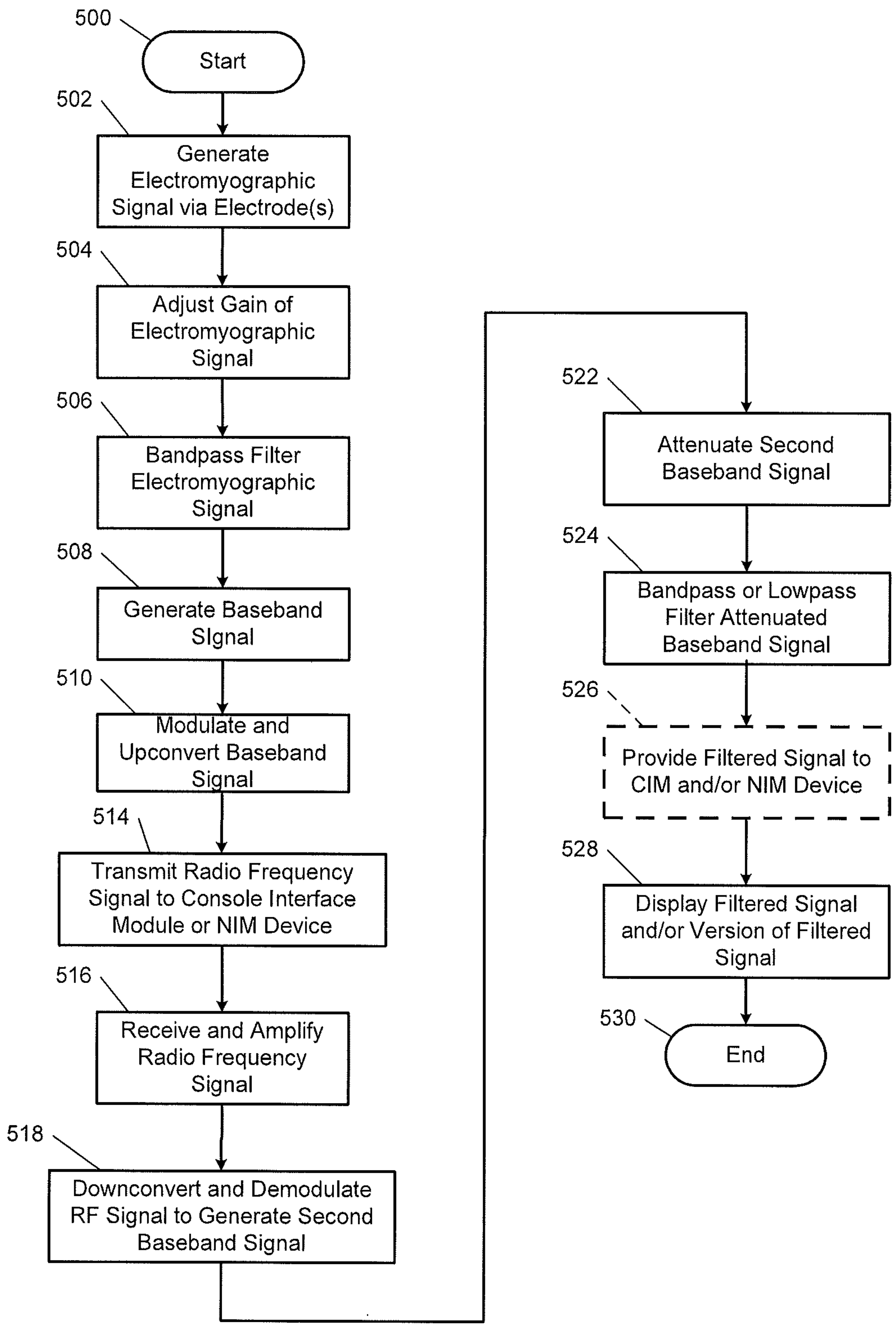
FIG. 20 illustrates a method of operating a sensor and a console interface module and/or NIM device in accordance with the present disclosure.
Figure 21:
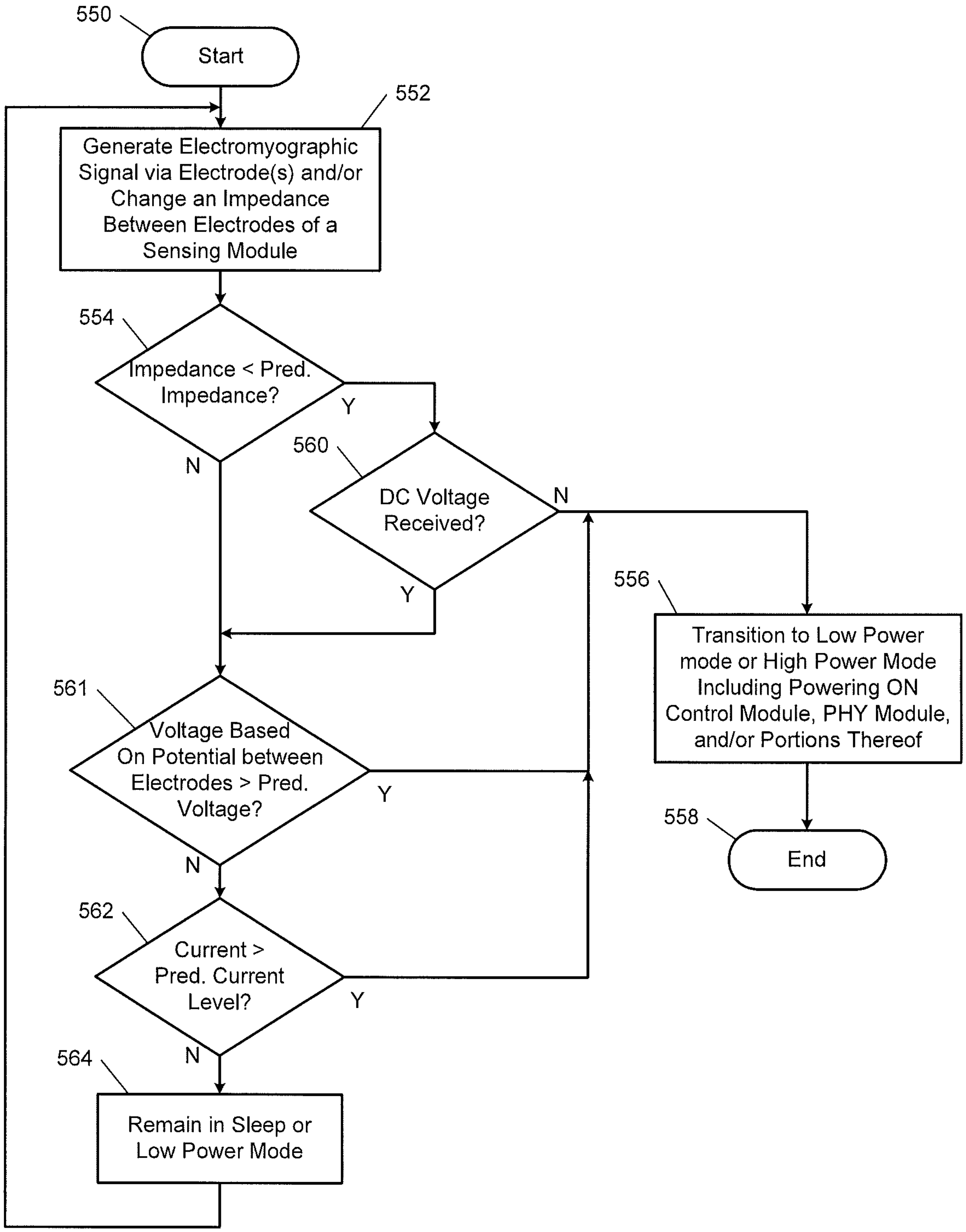
FIG. 21 illustrates a method of powering-up a sensor in accordance with the present disclosure.
Figure 22:
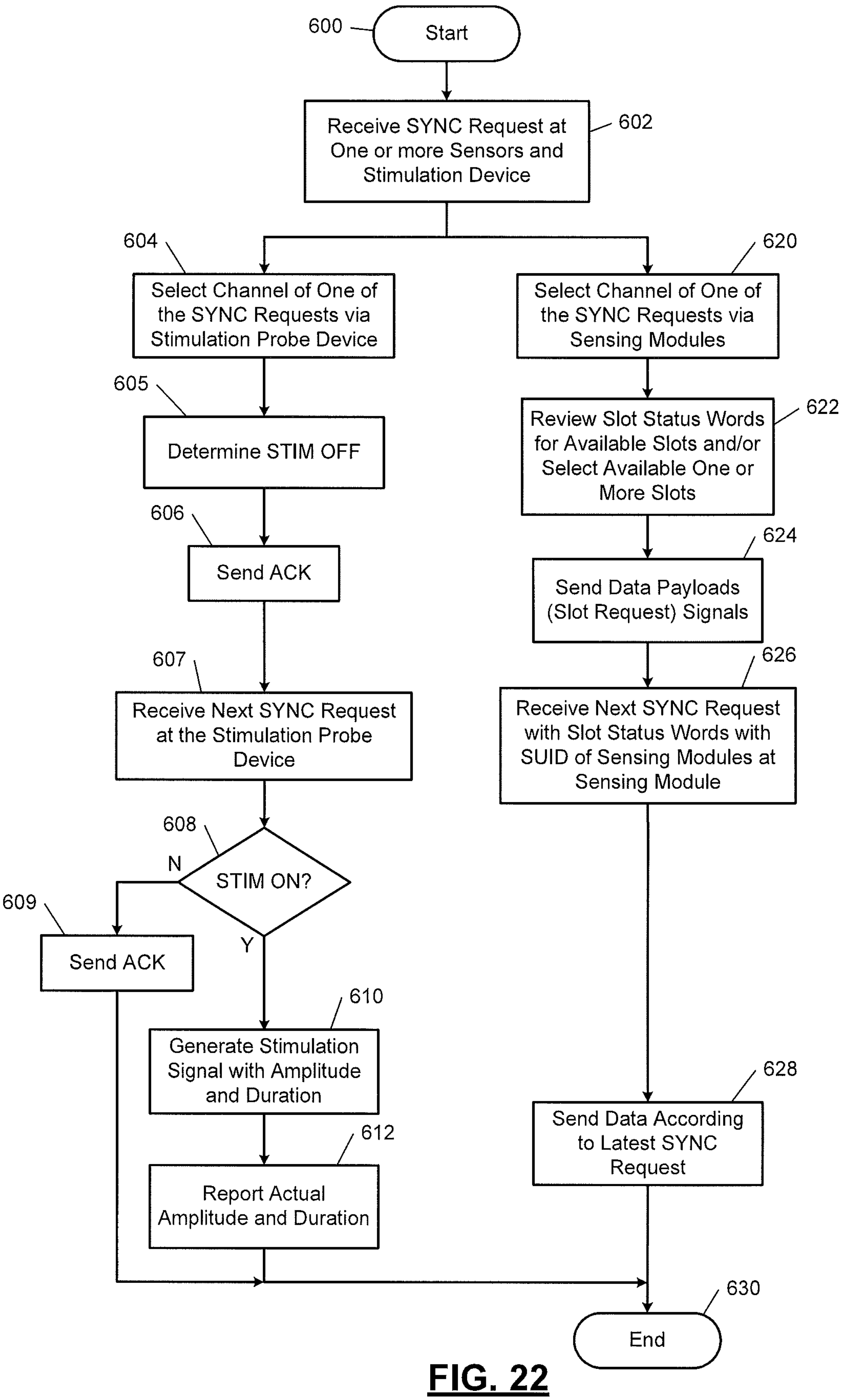
FIG. 22 illustrates a WNIM method of operating a stimulation probe device, one or more sensors, and a console interface module and/or NIM device in accordance with the present disclosure.

The systems, devices and modules disclosed herein may be operated using numerous methods, in addition to the methods described above, some additional example methods are illustrated in FIGS. 20-22. In FIG. 20, a method of operating a sensor and a CIM and/or NIM device is shown. Although the following tasks are primarily described with respect to the implementations of FIGS. 1-4 and 7A-13, the tasks may be easily modified to apply to other implementations of the present disclosure. The tasks may be iteratively performed.

The method may begin at 500. At 502, electromyographic signals are generated due to, for example, generation of a stimulation pulse. The electromyographic signals are detected by a control module (e.g., one of the control modules 56, 202) via electrodes. At 504, a gain module (e.g., the gain module 63) adjusts gain of the electromyographic signals. At 506, a filtering module (e.g., the filtering module 64) filters an output of the gain module. The filtering module may bandpass filter amplified electromyographic signals received from the gain module.

At 508, a BB module (e.g., the BB module 66) generates a BB signal based on the filtered and amplified electromyographic signals. At 510, a modulation module (e.g., the modulation module 78) modulates and upconverts the BB signal to generate an RF signal. At 514, a PHY module (e.g., one of the PHY modules 60, 204) and/or an amplification module (e.g., the amplification module 80) transmits the RF signal from the sensing module to a CIM and/or NIM device.

At 516, the CIM and/or NIM device receives the RF signal from the sensing module and amplifies the RF signal. At 518, a demodulation module (e.g., one of the demodulation modules 114, 176) downconverts the RF signal to generate a second BB signal. At 522, a BB module (e.g., one of the BB modules 128, 184) at the CIM and/or NIM device may attenuate the second BB signal, as described above. At 524, a filtering module (e.g., one of the filtering modules 126, 186) filters the attenuated second BB signal to generate a second filtered signal. This may include bandpass or low pass filtering.

At 526, the second filtered signal may be provided from the CIM to the NIM device. At 528, the NIM device may display the second filtered signal. As similar method as that shown with respect to FIG. 20 may be performed for data requested and received from a stimulation probe device. The method may end at 530.

In FIG. 21, a method of powering-up a sensor is shown. Although the following tasks are primarily described with respect to the implementations of FIGS. 1-4 and 7A-13, the tasks may be easily modified to apply to other implementations of the present disclosure. The tasks of FIG. 21 may be iteratively performed. The method may begin at 550.

At 552, an electromyographic signal is generated and/or an impedance between electrodes decreases due to attachment of the sensor to a patient. At 554, a power module (e.g., the power module 206) determines whether the impedance is less than a predetermined impedance (or threshold). If the impedance is less than the predetermined impedance, task 560 may be performed as shown, or alternatively task 556 may be performed. If the impedance is greater than or equal to the predetermined impedance, one or more of tasks 560, 561, 562, 564 may be performed. Although tasks 560, 561, 562, 564 are shown, any one of the tasks may not be performed and/or may be skipped. Also, tasks 560, 561, 562, 564 may be performed in a different order.

At 560, a control module (e.g., one of the control modules 56, 202) determines whether a DC voltage (may be referred to as an output voltage or output voltage signal) has been received from a power module (e.g., the power module 206), as described above. If a DC voltage is not received task 556 may be performed. If a DC voltage is received, task 561 is performed.

At 556, a sensing module of the sensor transitions to a LOW power mode or a HIGH power mode, which may include powering ON a portion, all, or a remaining portion of the control module and/or the PHY module. As an example, if a stimulation pulse is to be generated, the power module may transition to the HIGH power mode and power ON all or a remaining portion of the control module and/or the PHY module that are not already powered ON. Subsequent to task 556, the method may end at 558. Subsequent to task 556, the control module may proceed to, for example, task 504 of FIG. 20.

At 561, the power module may determine whether a voltage potential across the electrodes is greater than a predetermined voltage and/or has a magnitude that is greater than a predetermined magnitude. If the voltage potential is greater than the predetermined voltage and/or the magnitude is greater than the predetermined magnitude, task 556 may be performed, otherwise task 562 may be performed. In one embodiment, a stimulation probe device is used to activate sensors. The stimulation probe device generates an initial stimulation pulse to active the sensors. Additional stimulation pulses may be generated after the sensors are activated. The power module may detect the initial stimulation pulse by monitoring the voltage at the electrodes and/or amplified signals generated based on the voltage detected at the electrodes.

At 562, the power module may determine whether an amount of current received from one of the electrodes is greater than a predetermined current level. If the amount of current is greater than the predetermined current level, task 556 may be performed, otherwise task 564 may be performed. As stated above, a stimulation probe device may generate an initial stimulation pulse to activate sensors. The power module may detect the initial stimulation pulse by monitoring current received from one or more of the electrodes and/or amplified signals generated based on the current received from the one or more electrodes. In one embodiment, tasks 561 and/or 562 are performed and tasks 554 and/or 560 are not performed.

At 564, the power module refrains from generating the output voltage (or output signal) and the sensing module refrains from transitioning to the low power mode or the high power mode and remains in the sleep mode and/or low power mode. Subsequent to task 564, task 552 may be performed as shown or the method may end at 558.

In FIG. 22, a WNIM method of operating a stimulation probe device, one or more sensors, and a console interface module and/or NIM device is shown. Although the following tasks are primarily described with respect to the implementations of FIGS. 1-19, the tasks may be easily modified to apply to other implementations of the present disclosure. The tasks of FIG. 21 may be iteratively performed. The following tasks provide an example of initial power-ON and continuous and initial generation of periodic SYNC requests. The method may begin at 600.

At 602, sensors and one or more stimulation probe devices receive one or more SYNC requests from one or more CIMs and/or NIM devices. The control modules of the NIM devices may generate payload request signals requesting data payloads from sensors and stimulation probe devices. The control modules of the CIMs may each generate a SYNC request signal, which may be transmitted periodically (e.g., once every predetermined or SYNC) period).

At 604, a stimulation probe device selects a broadcast channel of one of the SYNC requests based on, signal strengths of the SYNC requests as received by the stimulation probe device. The stimulation probe device may hop through channels in a table to receive the SYNC requests. The broadcast channel of the SYNC request with the greatest signal strength is selected. The stimulation probe device may determine whether there is more than one stimulation probe device in the WNIM network of the selected SYNC request. If there is more than one stimulation probe device, an available time slot is selected by the stimulation probe device that is joining the WNIM network. This may be accomplished similar to how a sensor selects a time slot, as described above.

At 605, the stimulation probe device joining the WNIM network determines that a stimulation pulse is not to be generated based on corresponding status bits of the SYNC request of the selected broadcast channel. At 606, the stimulation probed device sends an ACK signal to the CIM and/or a NIM device of the selected broadcast channel.

At 607, the stimulation probe device receives an updated SYNC request from the CIM and/or NIM device of the selected broadcast channel.

At 608, the stimulation probe device that has joined the WNIM network determines whether a stimulation pulse is to be generated based on corresponding status bits of the updated SYNC request of the selected broadcast channel. If a stimulation pulse is requested to be generated, task 610 is performed, otherwise task 609 is performed. At 609, the stimulation pulse device sends an ACK signal to the CIM and/or NIM device of the selected broadcast channel.

At 610, the stimulation pulse device generates a stimulation pulse signal based on stimulation information words in the SYNC request. The stimulation pulse signal may be generated according to a delay period, an amplitude, and/or a duration provided in the SYNC request. At 612, the stimulation probe device reports a measured (or detected) amplitude and duration of the generated stimulation pulse to the CIM and/or the NIM device in a designated time slot of the periodic SYNC interval. This may occur in the same periodic SYNC interval as the SYNC request. Task 607 may be performed subsequent to task 612 or the method may end at 630 as shown.

At 620, each of the sensing modules selects a broadcast channel of a SYNC request with a greatest signal strength. The sensing modules may hop through channels in tables stored in the sensing modules to find and select the broadcast channel. At 622, each of the sensing modules of the sensors selects one or more time slots and/or checks statuses of time slots as indicated in the SYNC request of the selected broadcast channel. If a sensing module has not linked up previously to the CIM and/or the NIM device communicating the selected broadcast channel, then the sensing module selects an available time slot. If a sensing module has previously linked up to the CIM and/or NIM device, then the sensing module checks a status of the previously selected time slot to assure that the time slot is still designated to the sensing module. If the time slot is no longer designated to the sensing module, the sensing module may select another available time slot.

Multiple time slots may be designated to a sensing module based on a type of the corresponding sensor without the sensing module having previously requested multiple time slots. For example, if the sensor has multiple channels and/or is to be assigned multiple time slots, the CIM and/or NIM device may update slot status words accordingly based on a single slot request. The sensing module may then detect that multiple slots have been assigned during review of slot status words in a subsequent SYNC request.

At 624, the sensing modules may send data payloads in the respectively selected time slots. This serves dual purposes. In addition to providing data corresponding to signals detected at electrodes of the sensors, the sent data payloads serve as a request for the selected time slots. At 626, the sensing modules may receive a next updated SYNC request from the CIM and/or NIM device. The next updated SYNC request may indicate SUIDs of the sensing modules in slot status words. Task 626 may be performed while task 607 is performed. Tasks 626 and 607 may refer to the same updated SYNC request.

At 628, the sensing modules send data payloads in the designated time slots according to the updated SYNC request to the CIM and/or NIM device. Task 628 may be performed subsequent to task 610. Task 626 may be performed subsequent to task 628 or the method may end at 630 as shown. Although not shown in FIG. 22, some of the tasks may be iteratively performed for subsequent SYNC request signals and/or generation of additional stimulation pulses.

The above-described tasks of FIGS. 20-22 are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

Figure 23:
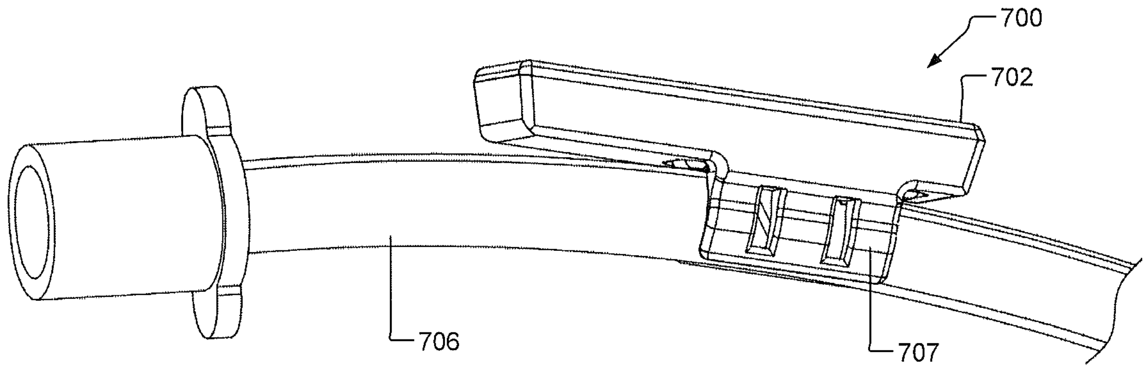
FIG. 23 is a side perspective view of a portion of another EMG endotracheal tube assembly in accordance with the present disclosure.
Figure 24:
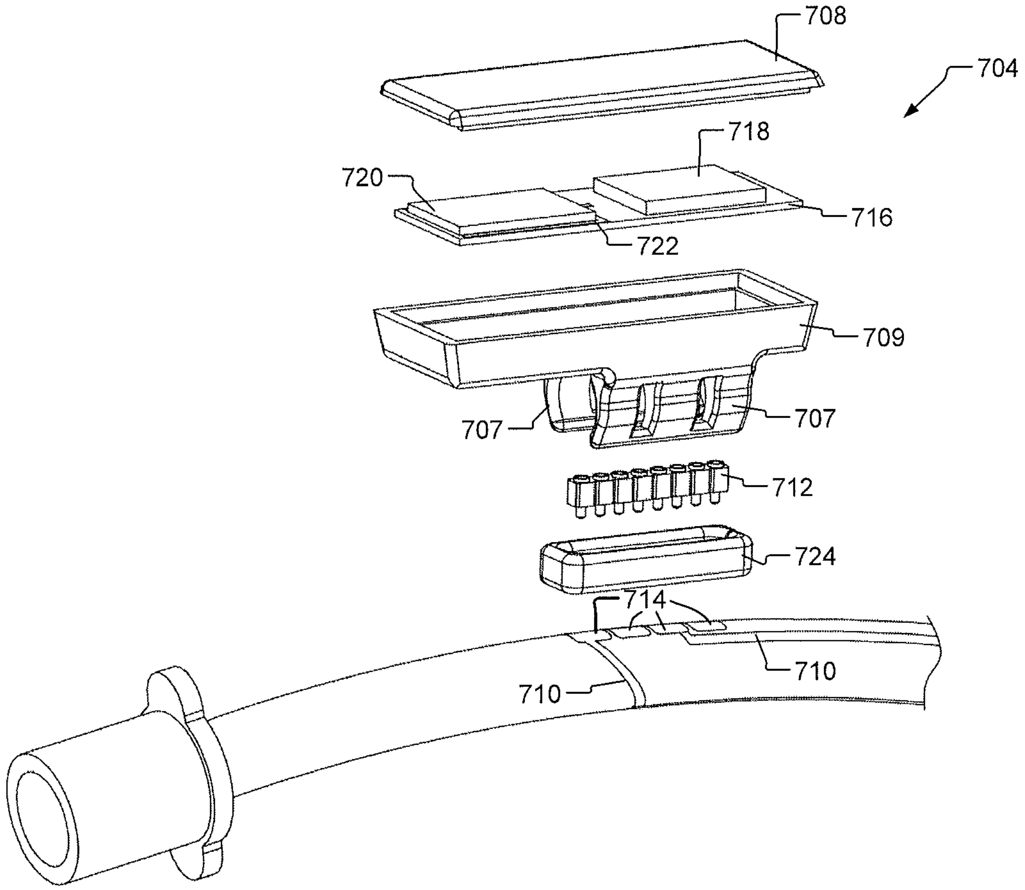
FIG. 24 an exploded view of a housing and corresponding electronic assembly of the EMG endotracheal tube assembly of FIG. 23.

FIGS. 23-24 show a portion 700 of another EMG endotracheal tube assembly including a housing 702 and a corresponding electronic assembly 704. The EMG tube assembly may replace or be used instead of the EMG tube assembly of FIGS. 8-13 and may include any of the modules described above with respect to any of the sensors disclosed herein. The housing 702 is connected to an endotracheal tube 706 via flanges 707. The housing 702 includes a top portion (or cover) 708 and a bottom portion 709. The EMG endotracheal tube assembly includes the housing 702 having the electronic assembly 704, electrodes 710, spring loaded pin elements 712, and contacts 714. The electronic assembly 704, electrodes 710, spring loaded pin elements 712, and contacts 714 may collectively be referred to as a sensor. The sensor may also include the housing 702, a substrate 716, a control (or sensing) module 718, a power source 720, an antenna 722, the spring loaded pin elements 712, and a sealing gasket 724.

The EMG endotracheal tube assembly of FIGS. 23-24 provides a low profile variant of the EMG endotracheal tube assembly of FIGS. 8-13. The power source (or battery) 720 has a “flat” or low-profile, which allows the housing 702 to have a lower profile than the housing 332. The power source 720 may be a “flatpack” battery, a lithium ion polymer (LiPON) battery, a wafer-scaled battery, or other planar packaged power source.

FIGS. 25-34 show a sensor assembly 750 incorporating a modular control (or sensing) module assembly 752, and including one or more of (i) a patch 754 with electrodes 755, and (ii) a pin electrode adaptor 756 with electrodes 758 and pin electrodes 760. The patch 754 may include a base having a flexible substrate and an adhesive layer with pads 762 (similar to the base 302 of FIGS. 7A-7B). The patch 754 provides electrical connections between the electrodes 755 and the pads 762. The pin electrode adaptor 756 provides electrical connections between the electrodes 758 and the pin electrodes 760. The patch 754 and the pin electrode adaptor 756 may include passive devices and may not include active (or smart) devices. The sensor assembly 750 or portions thereof may be used in replacement of any of the sensors shown in FIG. 1 and may include any of the modules described above with respect to any of the sensors disclosed herein.

The modular control module assembly 752 may be snapped onto the electrodes 755 of the patch 754 or may be snapped onto the electrodes 758 of the pin electrode adaptor 756. The modular control module assembly 752 and the pin electrode adaptor 756 may replace one of the sensors 12 of FIG. 1. The modular control module assembly 752 and the patch 754 may replace one of the sensors 13 of FIG. 1.

Figure 25:
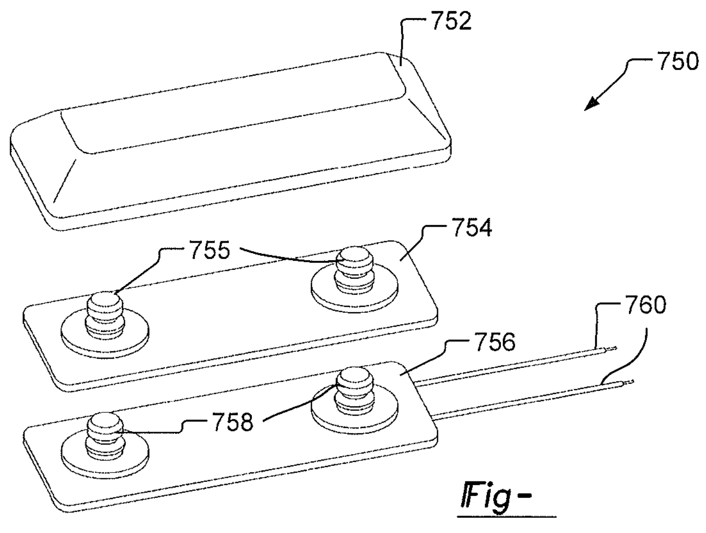
FIG. 25 is a perspective view of a sensor assembly incorporating a modular control module assembly in accordance with the present disclosure.
Figure 26:
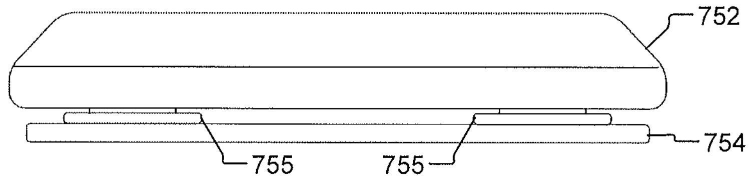
FIG. 26 is a side view of the modular control module assembly of FIG. 25 connected to a patch.
Figure 27:
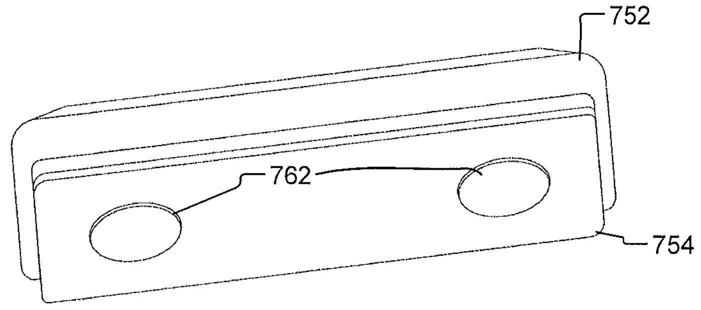
FIG. 27 is a bottom perspective view of the modular control module assembly of FIG. 25 illustrating pads of the patch.
Figure 28:
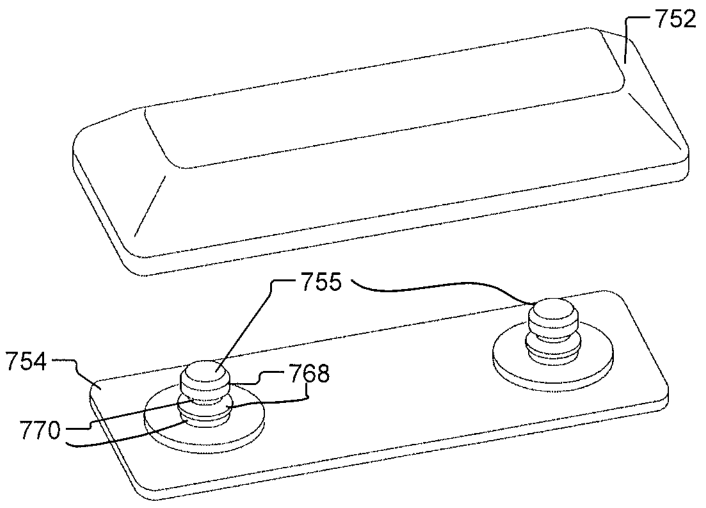
FIG. 28 is a perspective view of the modular control module assembly of FIG. 25 and the patch.
Figure 29:
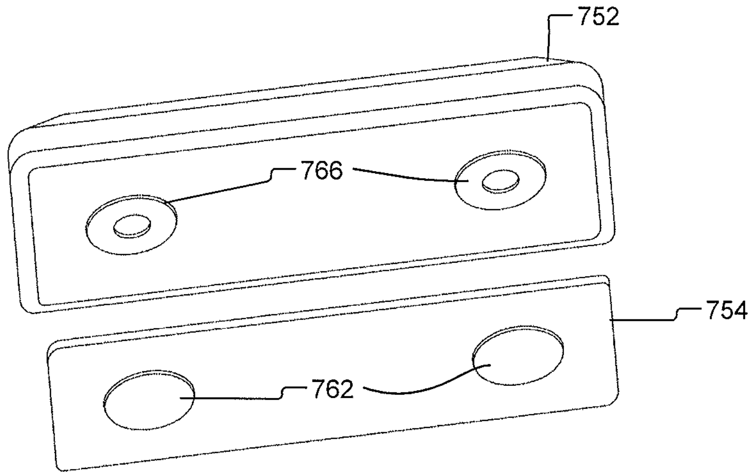
FIG. 29 is a bottom perspective view of the modular control module assembly of FIG. 25 and the patch.
Figure 30:
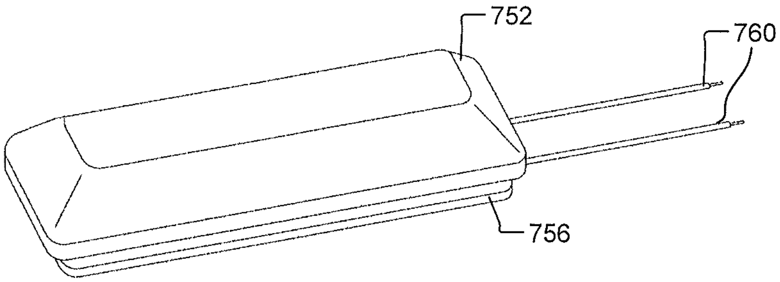
FIG. 30 is a perspective view of the modular control module assembly of FIG. 25 connected to a pin electrode adaptor in accordance with the present disclosure.
Figure 31:
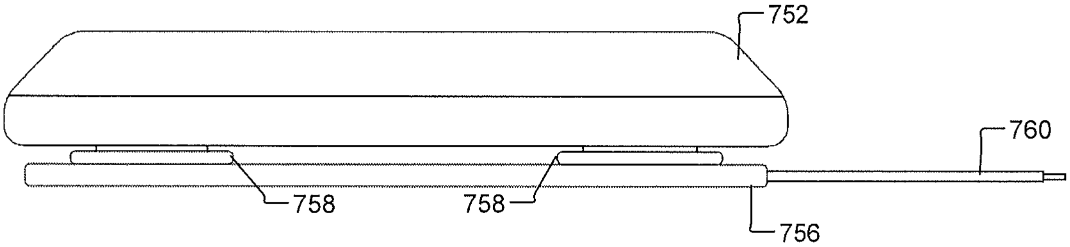
FIG. 31 is a side view of the modular control module assembly of FIG. 25 connected to the pin electrode adaptor.
Figure 32:
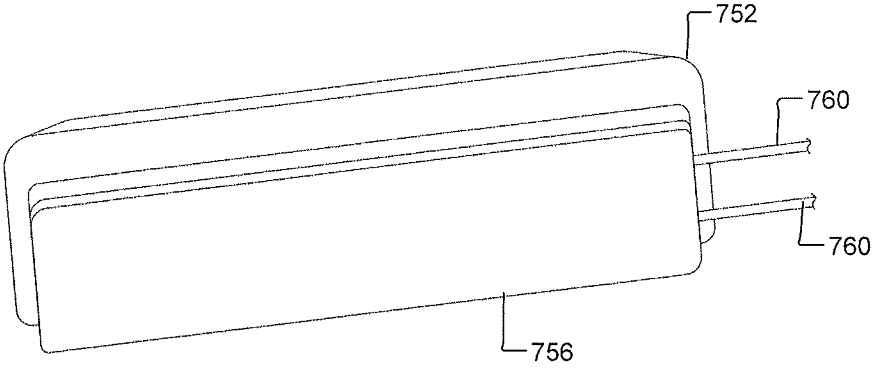
FIG. 32 is a bottom perspective view of the modular control module assembly of FIG. 25 connected to the pin electrode adaptor.
Figure 33:
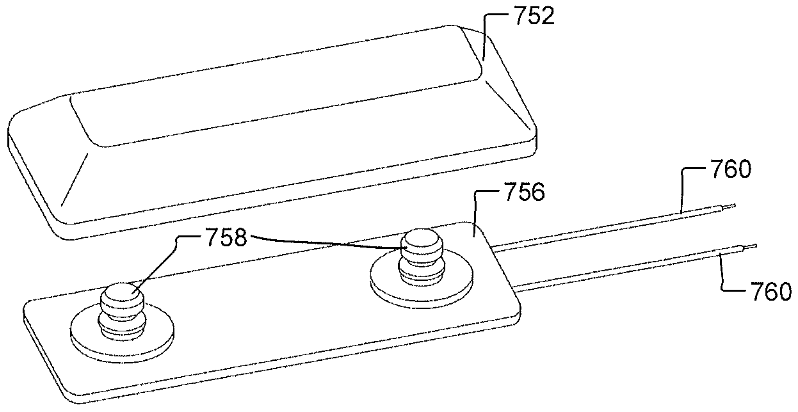
FIG. 33 is a top perspective view of the modular control module assembly of FIG. 25 and the pin electrode adaptor.
Figure 34:
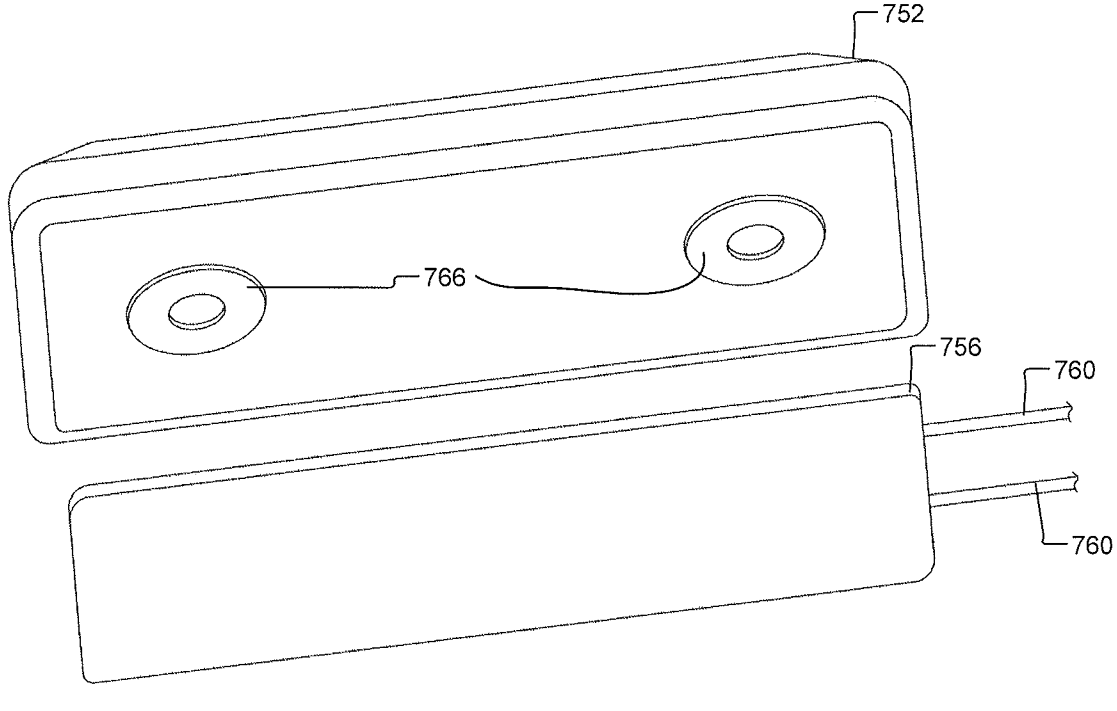
FIG. 34 is a bottom perspective view of the modular control module assembly of FIG. 25 and the pin electrode adaptor.

FIGS. 29 and 34 illustrate receiving connectors 766 that connect to the electrodes 755 of the patch 754 and the electrodes 758 of the pin electrode adaptor 756. The electrodes 755, 758 may be inserted into or plug into the receiving connectors 766. The electrodes 755, 758 may have one or more ribs (e.g., ribs 768) and recessed portions (e.g., recessed portions 770) that match corresponding portions of the receiving connectors 766, as shown in FIGS. 25, 28 and 33. The modular control module assembly 752 may be reusable and the patch 754 and the pin electrode adaptor 756 may not be reusable, as similarly described above with respect to the sensor of FIGS. 7A-7B. This minimizes system costs by allowing the modular control module assembly 752 to be reused multiple times, as opposed to being disposed of after being used once and/or for a single surgical procedure. In one embodiment, the modular control module assembly 752: is not reusable; may be connected to or include the patch 754 and/or the pin electrode adaptor 756; and may not snap onto the patch 754 or the pin electrode adaptor 756.

Figure 35:
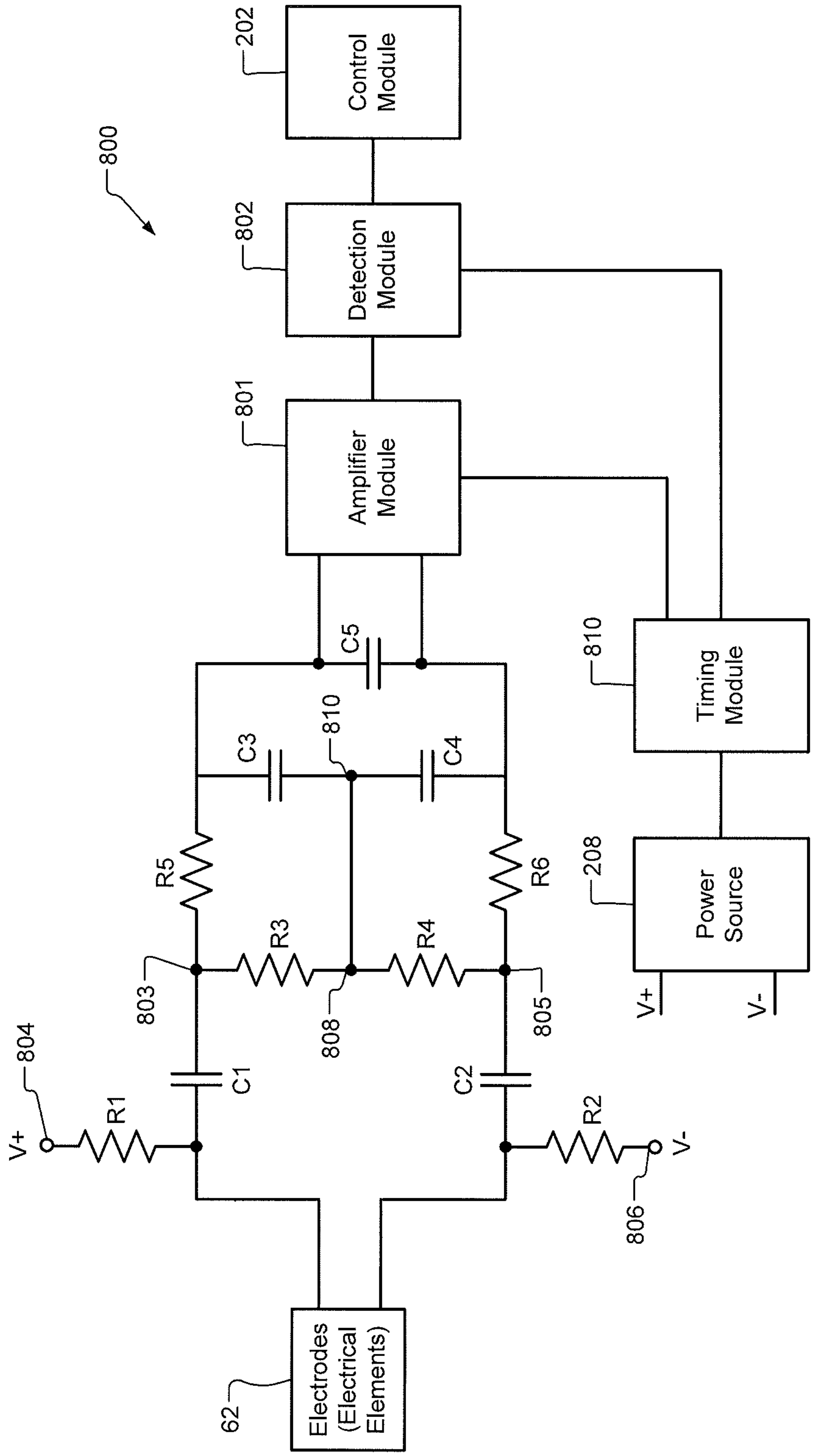
FIG. 35 is a circuit diagram of a portion of a power module in accordance with the present disclosure.

Referring now to FIG. 4 and FIG. 35, which shows a portion 800 (referred to as a front end circuit) of a power module (e.g., the power module 206 of FIG. 4). The portion 800 includes resistances R1, R2, which are connected to the electrodes 62. The resistance R1 is connected between one of the electrodes 62 and a voltage source providing voltage V+. The resistance R2 is connected between another one of the electrodes 62 and a voltage source or reference voltage V− (e.g., ground reference).

The portion 800 further includes capacitances C1, C2, resistances R3, R4, R5, R6, capacitances C3, C4, C5, an amplifier module 801, and a detection module 802. The capacitances C1, C2 are connected in series respectively with two of the electrodes 62 and are connected respectively between the resistances R1, R2 and the resistances R3, R4. The resistances R3, R4 are connected in series (i) between the capacitances C1, C2, and (ii) between the resistances R5, R6. The capacitance C1 and each of the resistances R3, R5 are connected to each other at terminal 803. The capacitance C2 and each of the resistances R4, R6 are connected to each other at terminal 805.

The resistances R1, R2, R3, R4 provide a voltage divider between voltage terminals 804, 806, which receive the voltages V+, V−. The resistances R5, R6 are connected in series respectively with the capacitances C1, C2 and are connected in series with capacitance C5. The capacitance C5 is connected between the resistances R5, R6. The capacitances C3, C4 are connected in series with each other and between the resistances R5 and R6. The capacitance C5 is connected across the capacitances C3, C4. A terminal 808 between resistances R3, R4 is connected to a terminal 810 between capacitances C3, C4. Each of the resistances R3, R4 are connected to each of the capacitances C3, C4 via the terminals 808, 810. The amplifier module 801 includes (i) two inputs that are connected respectively to ends of the capacitance C5, and (ii) an output that is connected to the detection module 802.

The capacitance C1 and resistance R3 operate as a first high pass filter. The capacitance C2 and resistance R4 operate as a second high pass filter. The resistance R5 and the capacitance C3 operate as a first low pass filter. The resistance R6 and the capacitance C4 operate as a second low pass filter.

During operation, if a patient is not connected to the electrodes 62, then an imbalance exists across the terminals 803, 805 such that a voltage at the terminal 803 is pulled up to the voltage V+ via resistance R1 and capacitance C1 and a voltage at the terminal 805 is pulled down to the voltage V− via resistance R2 and capacitance C2. The capacitances C1, C2 provide DC voltage blocking, but may exhibit leakage, which may be detected and amplified by the amplifier module 801. The voltage out of the amplifier module 801 is detected by the detection module 802. The detection module may generate a DC voltage when the patient is not connected to the electrodes 62. The DC voltage may then be provided to the control module 202 for detection that the patient is not connected to the electrodes 62. This is referred to as "lead-off" detection. As an example, a voltage difference between V+ and V− is between 2-5V.

If the patient is connected to the electrodes 62, then the imbalance across the terminals 803, 805 decreases because the voltage potential difference between the terminals 803, 805 decreases. This change in voltage, after filtering, is amplified by the amplifier module 802 and detected by the control module 202. The amplifier module 801 may include an amplifier for amplifying voltages across the capacitance C5. The detection module may not generate and/or provide the DC voltage to the control module 202 when the voltage potential difference between the terminals 803, 805 decreases.

There is a subtle effect, especially due to the DC blocking capacitances C1, C2. The resistances R1, R2, R3, R4, the capacitances C1, C2 and the voltage V+, V− are set to allow for lead-off detection and lead-on detection while minimizing current that could potentially pass to the patient via the electrodes 62. Current may follow a current path from the terminal 804 through the resistance R1, the capacitance C1, the resistances R3, R4, the capacitance C2 and then through the resistance R2 to the terminal 806. If there is, for example, 5 nano-amperes (nA) of current passing along this path, then there may be 100 micro-volts (μV) across the resistances R3, R4. If the amplifier module 801 provides a gain of 150, the output of the amplifier module 801 may be 15 milli-volts (mV) DC, which may be detected by the detection module 802.

The circuit shown in FIG. 35 may be used to alert a user that a sensor is disconnected from a patient and/or to wake up the sensor. In one embodiment, the portion 800, the power module 206, the control module 202, and/or a portion thereof periodically wakes up and checks whether a patient is attached to the electrodes 62. As an example, the power module 206 may periodically wake up and detect whether a patient is attached and inform the control module 202. As another example, the control module 202 may periodically wake up the power module 206 to perform this detection.

As yet another example, the portion 800 may include a timing module 810, which may receive power from the power source 208. The power source 208 may also provide the voltages V+, V− or the power module may generate the voltages V+, V-based on power from the power source 208. The timing module 810 may periodically wake up and supply power to the resistances R1, R2, the amplifier module 801 and/or the detection module 802. The detection module 802 may then detect whether a patient is attached to the electrodes 62. If the electrodes 62 are attached to a patient, the detection module may inform the control module 202 and/or power up the control module 202 and/or the PHY module 204.

The wireless communication and corresponding systems and devices disclosed herein provides several advantages. For example, the wireless communication and corresponding systems and devices provide improved signal-to-noise ratios due at least partially to elimination of large loops of wire associated with traditional systems. The wireless communication and corresponding systems and devices also electrically isolate a patient from monitoring devices. This provides improved safety by minimizing the amount of electrical current that may be supplied to a patient.

The wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium include nonvolatile memory circuits (such as a flash memory circuit or a mask read-only memory circuit), volatile memory circuits (such as a static random access memory circuit and a dynamic random access memory circuit), and secondary storage, such as magnetic storage (such as magnetic tape or hard disk drive) and optical storage.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C #, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

None of the elements recited in the claims is intended to be a means-plus-function element within the meaning of 35 U.S.C. § 112(f) unless an element is expressly recited using the phrase “means for”, or in the case of a method claim using the phrases “operation for” or “step for”.

What is claimed is:

1. A sensor, comprising:

a first processor operable to detect a first electromyographic signal generated from one or more electrodes configured to contact a patient, the first processor configured to generate a first voltage signal in response to the first electromyographic signal;

a transceiver operable to:

receive a synchronization (SYNC) request transmitted by a remote nerve integrity monitoring (NIM) device external to the sensor, wherein the remote NIM device is configured to signal a stimulation probe to generate one or more stimulation pulses to stimulate nerves of the patient;

responsive to the SYNC request, wirelessly transmit radio frequency signals based upon the first voltage signal to the remote NIM device;

periodically receive payload requests from the remote NIM device, wherein SYNC intervals exist between transmission of consecutive pairs of the SYNC requests and the SYNC requests allow synchronized timing in at least one of a respective plurality of time slots of payloads associated with the payload requests to prevent the radio frequency signals from being transmitted during a same time slot; and select at least one available time slot from the plurality of time slots and, prior to wirelessly transmitting the radio frequency signals, wirelessly transmit a join request to the remote NIM device;

a second processor adapted to operably couple to a power source and supply power to at least one of the first processor or the transceiver; and a housing configured to house at least the transceiver and the second processor.

2. The sensor of claim 1, wherein the one or more electrodes are a plurality of electrodes and include pad electrodes.

3. The sensor of claim 1, wherein the first processor is configured to connect to contacts on an endotracheal tube.

4. The sensor of claim 1, further comprising a temperature sensor configured to detect a change in temperature of the patient.

5. The sensor of claim 1, wherein the one or more electrodes includes pin electrodes.

6. The sensor of claim 1, further comprising:

an accelerometer configured to detect changes in acceleration and generate an acceleration signal in relation to any detected change in acceleration, wherein the transceiver is configured to wirelessly transmit the acceleration signal to the remote NIM device.

7. The sensor of claim 1, further comprising:

a front end circuit connected to the one or more electrodes;

an amplifier configured to amplify an output of the front end circuit; and a third processor configured to, based on an output of the amplifier (i) detect whether the one or more electrodes is attached to the patient, and (ii) generate an output signal indicating whether the one or more electrodes are attached to the patient, wherein the first processor is configured to generate the first voltage signal based on the output signal.

8. The sensor of claim 7, further comprising:

a timing circuit configured to periodically wake up and power on the amplifier and the third processor to check whether the one or more electrodes are attached to the patient.

* * * * *